(12) United States Patent
Foody et al.

(10) Patent No.: US 10,513,715 B2
(45) Date of Patent: Dec. 24, 2019

(54) WET OXIDATION OF BIOMASS

(71) Applicant: Iogen Corporation, Ottawa (CA)

(72) Inventors: Patrick J. Foody, Ottawa (CA); Brian Foody, Ottawa (CA)

(73) Assignee: Iogen Corporation, Ottawa, ON (CA)

( * ) Notice: Subject to any disclaimer, the term of this patent is extended or adjusted under 35 U.S.C. 154(b) by 0 days.

(21) Appl. No.: 15/762,226

(22) PCT Filed: Sep. 22, 2016

(86) PCT No.: PCT/CA2016/051103
§ 371 (c)(1),
(2) Date: Mar. 22, 2018

(87) PCT Pub. No.: WO2017/049394
PCT Pub. Date: Mar. 30, 2017

(65) Prior Publication Data
US 2019/0002930 A1 Jan. 3, 2019

Related U.S. Application Data

(60) Provisional application No. 62/232,116, filed on Sep. 24, 2015.

(51) Int. Cl.
| C12P 7/10 | (2006.01) |
| C10L 1/02 | (2006.01) |
| C13K 1/02 | (2006.01) |
| C12P 7/54 | (2006.01) |
| C13K 13/00 | (2006.01) |

(52) U.S. Cl.
CPC ........... *C12P 7/10* (2013.01); *C10L 1/02* (2013.01); *C12P 7/54* (2013.01); *C13K 1/02* (2013.01); *C13K 13/00* (2013.01); *C13K 13/002* (2013.01); *C10L 2200/0469* (2013.01); *C12P 2201/00* (2013.01); *Y02E 50/16* (2013.01)

(58) Field of Classification Search
CPC ........................................................ C10L 1/02
See application file for complete search history.

(56) References Cited

U.S. PATENT DOCUMENTS

| 2,782,243 | A | 2/1957 | Hess et al. |
| 3,562,319 | A | 2/1971 | Brink |
| 4,100,189 | A | 7/1978 | Mercier |
| 4,100,730 | A | 7/1978 | Pradt |
| 4,113,662 | A | 9/1978 | Wall |
| 4,384,897 | A | 5/1983 | Brink |
| 4,384,959 | A | 5/1983 | Bauer et al. |
| 4,421,939 | A | 12/1983 | Kiff et al. |
| 4,454,358 | A | 6/1984 | Kummer et al. |
| 4,497,967 | A | 2/1985 | Wan |
| 5,167,774 | A | 12/1992 | Berg |
| 5,221,357 | A | 6/1993 | Brink |
| 5,789,210 | A | 8/1998 | Ho et al. |
| 5,866,382 | A | 2/1999 | Hallborn et al. |
| 6,423,236 | B1 | 7/2002 | Shiota et al. |
| 6,475,768 | B1 | 11/2002 | Otero et al. |
| 6,509,180 | B1 | 1/2003 | Verser et al. |
| 6,555,350 | B2 | 4/2003 | Ahring et al. |
| 6,582,944 | B1 | 6/2003 | Hallborn et al. |
| 6,927,048 | B2 | 8/2005 | Verser et al. |
| 7,351,559 | B2 | 4/2008 | Verser et al. |
| 7,527,927 | B1 | 5/2009 | Ho et al. |
| 7,527,951 | B2 | 5/2009 | Londesborough et al. |
| 7,622,284 | B2 | 11/2009 | Op Den Camp et al. |
| 7,863,489 | B2 | 1/2011 | Johnston et al. |
| 8,232,440 | B2 | 7/2012 | Holtzapple et al. |
| 8,501,652 | B2 | 8/2013 | Johnston et al. |
| 8,506,716 | B2 | 8/2013 | Ahring et al. |
| 8,552,225 | B2 | 11/2013 | Horton et al. |
| 8,772,553 | B2 | 7/2014 | Wollrab et al. |
| 2005/0252858 | A1 | 11/2005 | Peyton et al. |
| 2007/0254348 | A1 | 11/2007 | Retsina et al. |
| 2012/0073199 | A1 | 3/2012 | Lewis |
| 2013/0232853 | A1 | 9/2013 | Peterson et al. |
| 2013/0345478 | A1 | 12/2013 | Wollrab et al. |
| 2014/0038252 | A1 | 2/2014 | Bell et al. |
| 2014/0054506 | A1 | 2/2014 | Melin et al. |
| 2014/0128642 | A1 | 5/2014 | Weiner et al. |
| 2014/0142351 | A1 | 5/2014 | Johnston et al. |
| 2014/0186903 | A1 | 7/2014 | Retsina et al. |

(Continued)

FOREIGN PATENT DOCUMENTS

| EP | 0 450 430 B1 | 6/1997 |
| EP | 2 191 061 B1 | 5/2013 |

(Continued)

OTHER PUBLICATIONS

Felby et al. ACS Symposium Series, 2003, 157-174.*
Agler et al., "Waste to bioproduct conversion with undefined mixed cultures: the carboxylate platform", Trends in Biotechnoogy, 2011, vol. 29, pp. 70-78.
Coutinho et al., "Carbohydrate-Active Enzymes: An Integrated Database Approach", Recent Advances in Carbohydrate Bioengineering—The Royal Society of Chemistry, Cambridge, pp. 3-12, 1999
Debellefontaine et al., "Wet air oxidation for the treatment of industrial wastes. Chemical aspects, reactor design and industrial applicaitons in Europe", Waste Management, 2000, 20, pp. 15-25.

(Continued)

*Primary Examiner* — Bin Shen
(74) *Attorney, Agent, or Firm* — Knobbe Martens Olson & Bear LLP

(57) ABSTRACT

A process for producing a transportation fuel from a lignocellulosic feedstock comprising subjecting a stream comprising lignin to a wet oxidation that produces low molecular weight carboxylic acids. These carboxylic acids and/or the corresponding esters are fed to a hydrogenation reaction or gas fermentation wherein they are converted to an alcohol. Heat from the wet oxidation may be supplied to any stage of the process in which heat is introduced.

23 Claims, 7 Drawing Sheets

(56) References Cited

U.S. PATENT DOCUMENTS

| | | |
|---|---|---|
| 2014/0199740 A1 | 7/2014 | Merrill et al. |
| 2015/0050707 A1 | 2/2015 | Gapes et al. |
| 2015/0133701 A1 | 5/2015 | Townsend et al. |

FOREIGN PATENT DOCUMENTS

| | | | |
|---|---|---|---|
| GB | 2 033 366 | A | 5/1980 |
| WO | 2006026863 | A1 | 3/2006 |
| WO | 2008041840 | A1 | 4/2008 |
| WO | 2009026722 | A1 | 3/2009 |
| WO | 2013128390 | A1 | 9/2013 |
| WO | 2014033256 | A1 | 3/2014 |
| WO | 2015131282 | A1 | 9/2015 |
| WO | 2016145528 | A1 | 9/2016 |
| WO | 2016145529 | A1 | 9/2016 |

OTHER PUBLICATIONS

Dhale et al., "Treatment of distillery waste after biogas generation: Wet oxidation", Ind. J. Chem. Technol., 2000, vol. 7, pp. 11-18.

Ghose, "Measurement of Cellulase Activities", Pure & Appl. Chem., 1987, vol. 59, No. 2, pp. 257-268.

Harris et al., "Stimulation of Lignocellulosic Biomass Hydrolysis by Proteins of Glycoside Hydrolase Family 61: Structure and Function of a Large, Enigmatic Family", Biochemistry 2010, 49, 3305-3316.

Lackner et.al., Capturing Carbon Dioxide from Air, Presented at First National Conference on Carbon Sequestration, Washington, DC, May 14-17, 2001, https://www.netl.doe.gov/publications/proceedings/01/carbon_seq/7b1.pdf.

Lynd et al., "Microbial Cellulose Utilization: Fundamentals and Biotechnology", Microbiology and Molecular Biology Review Sep. 2002, pp. 506-577.

Pradt, Louis A., "Wet oxidation Boiler—Incinerator". Zimpro Inc, retrieved from http://www.seas.columbia.edu/earth/wtert/sofos/nawtec/1978-National-Waste-Processing-Conference/1978-National-Waste-Processing-Conference-43.pdf on Mar. 6, 2018.

Zhang et al., "Hydrogenation of Ethyl Acetate to Ethanol over Ni-Based Catalysts Obtained from Ni/Al Hydrotalcite Like Compounds", Molecules 2010, 15, pp. 5139-5152, doi:10.3390/molecules15085139.

Zhu, Yongming., "Overview of Biomass Pretreatment Technologies", Novozymes 2011-18610-01.

International Search Report and Written Opinion in International Application No. PCT/CA2016/051103 (filed on Sep. 22, 2016), dated Dec. 6, 2016.

* cited by examiner

WET OXIDATION OF BIOMASS

This application is a national stage application of PCT/CA2016/051103 having an international filing date of Sep. 22, 2016, which claims benefit of U.S. provisional application No. 62/232,116 filed Sep. 24, 2015, which is incorporated by reference herein.

TECHNICAL FIELD

The instant invention relates generally to a method for producing an alcohol from biomass, and in particular to a method for producing a transportation fuel or fuel intermediate from biomass, wherein the method includes a wet oxidation.

BACKGROUND

The production of transportation fuels, primarily ethanol, from biomass continues to attract interest, due to the low cost and wide availability of biomass, and because ethanol produced from biomass (e.g., bioethanol) may be used to displace the use of fossil fuels. For example, ethanol used for a transportation fuel may be blended into gasoline at predetermined concentrations (e.g., 10%).

The production of bioethanol from first generation processes, wherein the biomass contains sugar that is readily fermented (e.g., sugar cane or sugar beets), or starch that is readily converted to sugar and then fermented (e.g., corn grain, barley, wheat, potatoes, cassava), is well known. In fact, the diversion of farmland or crops for first generation biofuel production has led to much debate about increased food prices and/or decreased food supplies associated therewith. In addition, there are concerns related to the energy and environmental impact of these production processes.

Second generation biofuels, also referred to as advanced biofuels, wherein the biomass contains lignocellulosic material and/or is obtained from agricultural residues or waste (e.g., corn cobs, corn stover (e.g., stocks and leaves), bagasse, wood chips, wood waste), may allay some of these concerns. For example, when bioethanol produced using second generation processes (i.e., also referred to as cellulosic ethanol) is derived from agricultural waste or residue, its production should not affect the food supply. In fact, tremendous effort is currently being expended to advance cellulosic ethanol production processes.

Lignocellulosic biomass typically contains cellulose, hemicellulose and lignin, each of which is present in plant cell walls. Cellulose (e.g., a type of glucan) is an unbranched chain polysaccharide including hexose (C6) sugar monomers (e.g., glucose). Hemicellulose is a branched chain polysaccharide derived from several sugars, which may include different pentose (C5) sugar monomers (e.g., xylose and arabinose) in addition to glucose. Lignin is a complex organic polymer, which typically includes cross-linked phenol polymers. Although generally insoluble in water at mild conditions, lignin may be soluble in varying degrees in dilute acid or base alkali. The ratio and/or structure of these components may vary depending on the source of the biomass.

The production of bioethanol from lignocellulosic biomass most often involves breaking down the cellulose and/or hemicellulose into the constituent sugars, which may then be fermented. Unfortunately, the cellulose, hemicellulose, and/or lignin found in lignocellulosic biomass is typically structured within the plant walls to resist degradation. For example, lignin, which may be the most recalcitrant component of lignocellulosic biomass, is believed to be tightly bound to the cellulose and/or hemicellulose.

In general, lignocellulosic biomass may be broken down into sugars in one or more stages, wherein at least one stage includes a chemical hydrolysis (e.g., which may include the addition of acid, base, and/or heat) and/or an enzymatic hydrolysis (e.g., which includes using enzyme(s)).

For example, one common approach to converting lignocellulosic biomass to sugar(s) includes (a) a pretreatment stage, followed by (b) an acid or enzymatic hydrolysis. In this approach, the goal of the pretreatment stage is to break down the lignin structure and/or disrupt the crystalline structure of the cellulose, so that the acids or enzymes used in the hydrolysis can easily access and hydrolyze the cellulose to sugar.

In general, pretreatment methods that improve the rate and/or yield of sugar in the subsequent hydrolysis (e.g., by liberating the cellulose from the lignin and/or by making the cellulose more accessible) may be used. Some examples of suitable pretreatments include acid pretreatment, alkali pretreatment, autohydrolysis (e.g., hot water extraction that does not require the addition of acid or base) steam explosion, and wet oxidation. For example, dilute acid pretreatment is believed to hydrolyze the hemicellulose component of the feedstock to yield xylose, glucose, galactose, mannose and/or arabinose, whereas alkali pretreatments are believed to cleave hydrolysable linkages in lignin and/or glycosidic bonds of polysaccharides (e.g., thus disrupting lignin structure and/or reducing crystallinity of cellulose). Accordingly, acid pretreatment, alkali pretreatment, and autohydrolysis may be considered forms of chemical hydrolysis.

Although treating lignocellulosic biomass with a mild acid pretreatment (e.g., a high temperature, short residence time) has been proven useful in terms of hydrolyzing the hemicellulose component to produce xylose, glucose, and/or arabinose, chemical hydrolysis of the cellulosic component typically requires relatively harsh conditions (e.g., dilute acid under high heat and high pressure, or more concentrated acid at lower temperatures and atmospheric pressure). Unfortunately, these relatively harsh conditions may produce toxic degradation products that can interfere with the fermentation process. Accordingly, it is advantageous if the hydrolysis following the pretreatment stage is enzymatic rather than solely chemical (e.g., acid).

In each case, the enzymatic and/or chemical hydrolysis is typically followed by a fermentation stage, which for example uses one or more yeasts or bacteria to convert the sugar(s) produced by the hydrolysis to an alcohol (e.g., ethanol). Yeast cells, in particular, have experienced widespread use in cellulosic ethanol processes because these naturally occurring or genetically modified microorganisms are particularly efficient at converting sugars such as glucose and xylose to ethanol. In fact, yeast cells have been used in biotechnology for hundreds of years to produce ethanol.

Despite the fact that sugars are natural intermediates in the biological and chemical conversion of lignocellulosic biomass, and that a properly selected combination of pretreatment and enzymes can enable high yields of sugar from both hemicellulose and cellulose, there may be some challenges to this type of approach. For example, much effort has focused on optimizing the pretreatment and/or hydrolysis stages of the process to make it cost competitive with corn-based ethanol. Another challenge is that a portion of the biomass will not be converted to ethanol. For example, it is well known that some lignin typically remains after pretreatment/hydrolysis (e.g., insoluble lignin and/or solubilized lignin). For example, in some cases the remaining lignin may be burned to provide on-site power, thus recovering some energy from the biomass.

Apart from the biochemical process discussed above, another second generation approach to producing biofuels is to use a thermal process. In particular, the lignocellulosic biomass may be heated at high temperature in the absence (i.e., pyrolysis) or presence (i.e., gasification) of oxygen, air and/or steam. Pyrolysis of biomass may be used to produce bio-oil, whereas gasification (i.e., which occurs without combustion) may be used to produce syngas. Syngas, which may include carbon monoxide (CO), hydrogen ($H_2$) and/or carbon dioxide ($CO_2$), may be converted to a biofuel (e.g., via a Fischer-Tropsch reaction) or used as a biofuel. For example, in one approach, syngas is converted to mixed alcohols using a catalyst. In another approach, syngas is subjected to a gas fermentation to provide ethanol from CO, $CO_2$ and/or $H_2$. Unfortunately, some of the energy stored in the sugar polymers may be lost in the thermal process (e.g., a portion of the biomass may not gasify). In addition, these thermal processes may be difficult to operate and/or may require a high energy investment (e.g., especially if using a Fischer-Tropsch process), which means that these processes may not yet be economical (e.g., relative to the biochemical approach discussed above) and/or do not reduce greenhouse gas emissions.

SUMMARY

In accordance with one embodiment of the instant invention, ethanol is produced from biomass using a process that includes a wet oxidation. In one embodiment, the process does not require a pretreatment, an enzymatic hydrolysis, or a fermentation, in order to produce ethanol.

Advantageously, the process may use any type of biomass, including secondary streams from first and/or second generation ethanol production plants, as feed to the wet oxidation. Without being limiting, the wet oxidation may form a step within a process dedicated to producing alcohol from biomass. The wet oxidation may be included at any stage of the process, including downstream stages or ancillary stages of the process. In one embodiment, the process may be used within an existing first or second generation ethanol production plant to increase ethanol yield and/or simplify water recycling. For example when the process uses secondary streams from an existing first or second generation ethanol plant as feed to the wet oxidation, the wet oxidation may simultaneously produce the intermediate(s) for producing ethanol and treat the secondary stream, thus producing treated water that may be recycled back into the plant.

In one embodiment, the wet oxidation converts at least a portion of the biomass to acetic acid, acetate, or mixtures thereof, which in turn is converted to an alcohol (e.g., ethanol) via addition of hydrogen. Since the wet oxidation may require and/or generate significant amounts of heat, excess heat from the wet oxidation may be used elsewhere within the plant and/or process (e.g., to recover the ethanol). Accordingly, in certain embodiments, the method may be simpler, use less equipment, have lower costs, and require less energy. Alternatively, the method may provide a useful alternative to known methods.

In accordance with one aspect of the invention there is provided a method of producing a transportation fuel or fuel intermediate comprising: (i) subjecting biomass to a wet oxidation that produces at least one of acetic acid, acetate, and carbon dioxide, the biomass comprising lignin; (ii) converting the at least one of acetic acid, acetate, and carbon dioxide to an alcohol; (iii) recovering the alcohol and providing it for use as a transportation fuel or fuel intermediate.

In accordance with one aspect of the invention there is provided a process for producing a transportation fuel or fuel intermediate comprising: treating lignocellulosic feedstock in one or more steps to provide a sugar; fermenting the sugar to produce a fermentation product; recovering the fermentation product to provide a first stream comprising the fermentation product and a second other stream from which the fermentation product has been at least partially removed; subjecting a stream from the process to a wet oxidation to produce at least one of acetic acid, acetate, and carbon dioxide, the stream from the process comprising lignin; converting the at least one of acetic acid, acetate, and carbon dioxide to an alcohol.

In accordance with one aspect of the invention there is provided a process for converting lignocellulosic feedstock to ethanol comprising: (i) pretreating lignocellulosic feedstock with a sulfur containing acid; (ii) hydrolyzing the pretreated lignocellulosic feedstock to provide a sugar; (iii) fermenting the sugar to produce ethanol; (iv) subjecting a stream comprising lignin to a wet oxidation, the wet oxidation producing acetic acid, acetate, or a combination thereof; and (v) converting the acetic acid, acetate, or combination thereof produced by the wet oxidation to ethanol.

In accordance with one aspect of the invention there is provided a method for processing lignocellulosic feedstock comprising: (i) treating lignocellulosic feedstock in one or more steps to provide a sugar; (ii) fermenting the sugar to produce ethanol; (iii) subjecting a stream from the process to a wet oxidation, the wet oxidation producing acetic acid; and (iv) introducing hydrogen and at least one of the acetic acid and an ester of the acetic acid to a reactor to produce ethanol.

In accordance with one aspect of the invention there is provided a method for producing an alcohol comprising: (i) feeding biomass to a first reactor, the first reactor including at least one inlet for feeding a stream comprising an oxidant into the first reactor; (ii) subjecting the biomass in the first reactor to a wet oxidation reaction at a temperature above about 100° C. such that at least a portion of the biomass is converted to a carboxylic acid; (iii) recovering a compound from a stream comprising effluent from the first reactor, the compound comprising the carboxylic acid or an ester of the carboxylic acid; (iv) introducing the compound to a second other reactor, the second other reactor including at least one inlet for feeding a stream comprising hydrogen into the second reactor; (v) subjecting the compound to a reaction including hydrogen in the second reactor; and (vi) recovering an alcohol produced by the reaction in the second reactor.

In accordance with one aspect of the invention there is provided a process for producing bioethanol comprising: feeding a secondary stream from at least one of a first generation ethanol process, a second generation ethanol process, and a pulp and paper process to a wet oxidation reactor; conducting a wet oxidation reaction at a temperature above about 100° C. such that at least a portion of the biomass in the secondary stream is converted to a carboxylic acid; recovering at least one of the carboxylic acid and an ester of the carboxylic acid from a stream comprising effluent from the wet oxidation reactor; converting the at least one of the carboxylic acid and an ester of the carboxylic acid to an alcohol; and recovering the alcohol.

BRIEF DESCRIPTION OF DRAWINGS

Exemplary embodiments will now be described in conjunction with the drawings in which.

It will be noted that throughout the appended drawings, like features are identified by like reference numerals.

DETAILED DESCRIPTION

Figure 1:
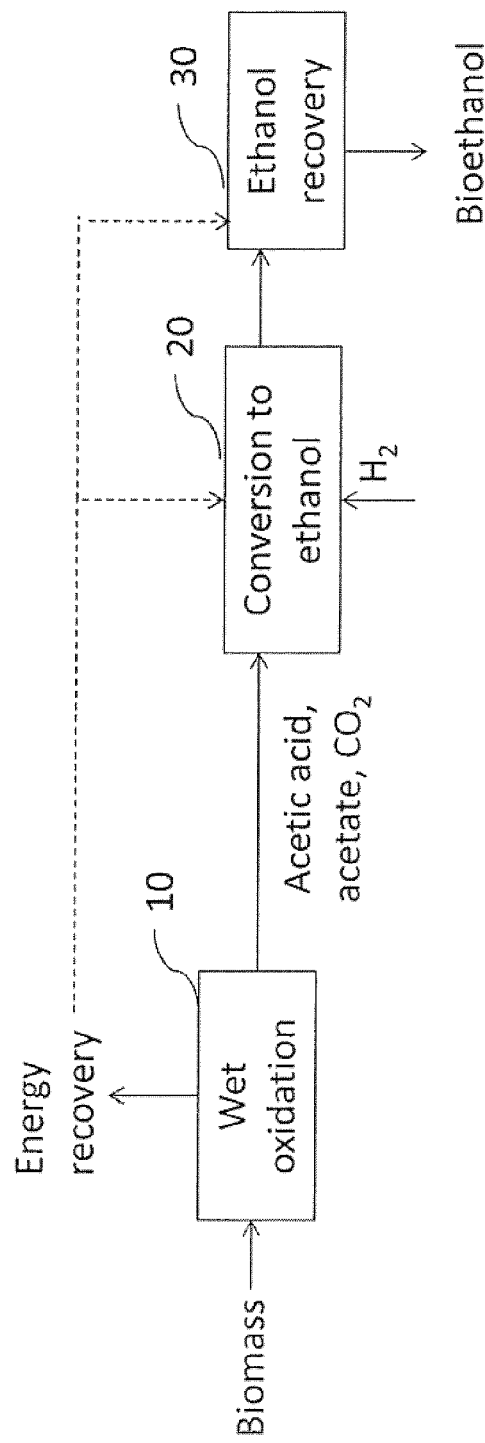
FIG. 1 is a flow diagram of a method in accordance with one embodiment of the invention.

Referring to FIG. 1, there is shown a method in accordance with one embodiment of the invention. Biomass is fed to a wet oxidation 10 that produces one or more intermediates/products (e.g., acetic acid, acetate, and/or carbon dioxide). At least one of these intermediates/products is fed to an alcohol conversion 20 wherein it is converted to an alcohol. The alcohol produced is concentrated and/or purified in recovery 30. The recovered alcohol may then be provided as a transportation fuel (e.g., shown as bioethanol) and/or fuel intermediate. For example, in one embodiment the ethanol is blended with gasoline for use as a transportation fuel.

Biomass

Biomass refers to biological material derived from living, or recently living organisms. For example, biomass includes plant matter grown for use as biofuel, plant or animal matter used for the production of fibres, chemicals, or heat, and/or biodegradable wastes. In addition, the term biomass includes processed biomass (e.g., feedstock that has been subjected to one or more processing steps). For example, processed biomass may include biomass sourced from a secondary stream in a first generation ethanol production plant, a secondary stream in a second generation ethanol production plant, a secondary stream in a pulp and paper mill, and/or a secondary stream from another process. The phrase "secondary stream" includes streams that branch off from and/or are otherwise sourced from the main stream and/or streams that provide the primary product(s).

In some embodiments, the biomass fed to the wet oxidation includes lignocellulosic feedstock or is derived from lignocellulosic feedstock.

By the term "lignocellulosic feedstock", it is meant any type of feedstock containing at least cellulose and lignin (e.g. may contain non-woody plan biomass and/or feedstock derived from plant biomass). For example, in one embodiment the combined content of cellulose, hemicellulose and lignin in lignocellulosic feedstock is greater than 25 wt % (w/w). In one embodiment, sucrose, fructose and/or starch are also present, but in lesser amounts than cellulose and hemicellulose.

By the phrase "biomass derived from lignocellulosic feedstock" or "lignocellulosic derived biomass", it is meant processed biomass that has been obtained, directly or indirectly, from a process that processes lignocellulosic feedstock.

Some examples of lignocellulosic feedstock and/or lignocellulosic derived feedstock include (i) energy crops; (ii) residues, byproducts or waste from the processing of plant biomass in a facility or feedstock derived therefrom; (iii) agricultural residues; (iv) forestry biomass; (v) waste material derived from pulp and paper products; (vi) pulp and paper waste; and/or (vii) municipal waste including components removed from municipal waste.

Energy crops include biomass crops such as grasses, including C4 grasses, such as switch grass, energy cane, sorghum, cord grass, rye grass, miscanthus, reed canary grass, C3 grasses such as Arundo donax, or a combination thereof.

Residues, byproducts or waste from the processing of plant biomass in a facility of feedstock derived therefrom include residues remaining after obtaining sugar from plant biomass such as sugar cane bagasse, sugar cane tops and leaves, beet pulp, or residues remaining after removing sugar from Jerusalem artichoke or residues remaining after grain processing, such as corn fiber, corn stover or bran from grains.

Agricultural residues include, but are not limited to soybean stover, corn stover, sorghum stover, sugar cane tops and/or leaves, rice hulls, rice straw, barley straw, corn cobs, wheat straw, canola straw, oat straw, rye straw, oat hulls, corn fiber, and corn cobs. As used herein, straw refers to the stem, stalk and/or foliage portion of crops remaining after the removal of starch and/or sugar containing components for consumption, whereas stover includes the stalk and foliage portion of crops after the removal of starch and/or sugar containing components of plant material for consumption.

Forestry biomass includes recycled wood pulp fiber, sawdust, hardwood, softwood, trimmings and/or slash from logging operations. Pulp and paper waste includes waste from chemical pulping such as black liquor, spent sulfite liquor, sludge and/or lines.

Municipal waste includes post-consumer material or waste from a variety of sources such as domestic, commercial, institutional and/or industrial sources. For example, the term includes refuse from waste collection and/or sewage sludge.

In one embodiment, the biomass includes fresh lignocellulosic feedstock, partially dried lignocellulosic feedstock, fully dried lignocellulosic feedstock, or a combination thereof. In one embodiment, the lignocellulosic feedstock is treated with a chemical and stored for a prolonged length of time. In one embodiment, the lignocellulosic feedstock is produced by plant breeding or by genetic engineering. In one embodiment, the biomass includes a mixture of fibers that originate from different kinds of plant materials, including mixtures of cellulosic and non-cellulosic feedstocks.

In one embodiment, the biomass will have been subject to size reduction. For example, in one embodiment, lignocellulosic feedstock having an average particle size less than about 6 inches is not subjected to size reduction, whereas feedstock having an average particle size greater than about 6 inches is subjected to size reduction. Some examples of suitable size reduction methods include, but are not limited to, milling, grinding, agitation, shredding, compression/expansion, or other types of mechanical action. Size reduction by mechanical action may be performed by any type of equipment adapted for the purpose, for example, but not limited to, hammer mills, tub-grinders, roll presses, refiners and hydrapulpers. In one embodiment, at least 90% by volume of the particles produced from the size reduction may have a length less than between about 1/16 and about 6 inches. One example of suitable equipment for the particle size reduction is a hammer mill, a refiner or a roll press as disclosed in WO 2006/026863.

Although size reduction may not be required for the wet oxidation, it may facilitate the wet oxidation and/or be advantageous with regards to transporting the biomass to the wet oxidation 10, particularly when the biomass includes agricultural residues or forestry biomass. In general, the biomass may have been subjected to a size reduction if the biomass is obtained from a stream of a first or second generation ethanol production process or from another process such as a pulp and paper process (i.e., processed lignocellulosic feedstock). Optionally, before, during or subsequent to size reduction, the biomass may be slurried in liquid (e.g., water), which allows the feedstock to be pumped. The desired weight ratio of water to dry lignocellulosic feedstock solids in the slurry is determined by factors such as pumpability, pipe-line requirements, and other practical considerations. For example, in one embodiment, the consistency of the biomass is between 1% and 20% or between about 1% and about 10%. In addition to improving pumpability, providing a relatively low consistency feed advantageously provides the water required for the wet oxidation. However, it should be understood that the feedstock need not be slurried, but rather could be led to the wet oxidation 10 without prior addition of liquid. This would generally occur when the required water is added to the wet oxidation tank separately.

In another embodiment, the biomass fed to the wet oxidation includes a sugar or starch crop or is derived from a sugar or starch crop. For example, some examples of suitable sugar and/or starch crops include sugar beet, sugar cane, sweet sorghum, potatoes, cassava, vegetable waste, and grains such as corn, barley, wheat, triticale, and grain sorghum. Although, the sugars found in these sugar and starch crops are readily converted to ethanol, feeding waste, residue, and/or by-product streams from these first generation ethanol production plants to the wet oxidation 10 may advantageously increase overall ethanol yield.

In general, when the biomass fed to the wet oxidation is sourced from a secondary stream from a first generation ethanol production process (e.g., including corn whole stillage), a secondary stream from a second generation ethanol production process (e.g., including still bottoms, lignin solids, and/or washing solutions), or a secondary stream from another production plant (e.g., solid residues, wastewater effluent, wastewater sludge, woodyard waste, causticizing wastes), the biomass may be considered to be processed biomass (e.g., biomass derived from a lignocellulose feedstock or biomass derived from a sugar or starch crop). Notably, secondary streams in first generation ethanol production processes (e.g., whole stillage) may also include lignocellulosic material. The phrase "first generation ethanol production process", as used herein, refers to ethanol production processes wherein the ethanol is derived from what may be considered food crop. For example, corn, wheat, and sugarcane are some examples of feed used in first generation ethanol production processes. In contrast, in second generation ethanol production processes the ethanol may be derived from non-food crops (e.g., agricultural residues).

In one embodiment, the biomass is raw biomass. The phrase "raw biomass", as used herein, refers to biomass that is not subjected to a chemical pretreatment and/or chemical processing after it is obtained from the provider, but may include biomass to which water and/or heat has been added and/or that has been subject to mechanical treatment (e.g., size reduction).

In one embodiment, the biomass is processed biomass. In one embodiment, the biomass is sourced from a pulp and paper mill, a sugar cane mill, and/or a cellulosic ethanol plant. In one embodiment, the biomass is sourced from a secondary stream of a cellulosic ethanol plant that includes lignin solids, still bottoms, or wash solution. In one embodiment, the biomass fed to the reactor is an unfiltered and undigested still bottoms stream. The phrase "and/or", as used herein, should be understood to refer to either or both of the elements so conjoined. The phrase "at least one" in reference to a list of one or more elements, should be understood to refer to at least one element selected from any one or more of the elements in the list of elements, but not necessarily including at least one of each and every element specifically listed within the list of elements. Thus as a non-limiting example, the phrase "at least one of A and B" may refer to at least one A with no B present, at least one B with no A present, or at least one A and at least one B in combination.

Wet Oxidation

In general, the term "wet oxidation" refers to an aqueous phase oxidation, which may take place through a family of related oxidation and hydrolysis reactions.

Wet oxidation of dissolved or suspended organic substances may be accomplished by heating a solution or slurry to a predetermined temperature in a closed and/or pressure controlled vessel into which an oxidant is introduced. Some examples of suitable oxidants include air, oxygen, ozone, and hydrogen peroxide. Alternatively, another oxidant is used. It is particularly advantageous to use oxygen and/or air as the oxidant due to cost and simplicity (e.g., use of an air compressor). For example, many wet oxidations systems are wet air oxidation (WAO) systems. In some cases, it may be advantageous to use an increased concentration of oxygen. In one embodiment, the oxidant is an oxygen stream purified from air.

In general, a wet oxidation may be run at elevated temperatures and pressures. For example, when the oxidant is air, the temperature within the reaction vessel may be greater than about 100° C., whereas the pressure within the closed vessel may be greater than ambient pressure (e.g., the initial partial pressure of the oxygen within the closed vessel may be equal to or may exceed the ambient partial pressure of oxygen). In one embodiment, the pressure within the closed vessel is selected and maintained at a value sufficiently high to prevent excessive evaporation.

Referring again to FIG. 1, biomass is fed to wet oxidation 10 either as a solution, slurry (e.g., high or low consistency), or as dry fiber. In embodiments wherein the biomass has a high consistency and/or includes dry fiber, an appropriate amount of water and/or steam may be added to the reaction vessel to allow wet oxidation to occur. Feeding a low consistency slurry to the wet oxidation is advantageous for case of pumpability. For example, in one non-limiting embodiment, the stream subjected to wet oxidation 10 may contain at least 80% by weight water (w/w) or at least 90% by weight water (w/w). The stream of biomass may include raw biomass, pretreated biomass, and/or processed biomass (e.g., biomass obtained from secondary streams in a pulp or ethanol production process).

In general, the wet oxidation conditions will be selected to achieve a suitable level of oxidation and may depend on the type of biomass, the selected oxidant and/or reaction temperature that is utilized. As will be appreciated by those of skill in the art, higher concentrations of oxidant, higher reaction temperatures, and longer residence times within the reactor typically correspond to a more complete oxidation. Other factors that may affect the level of oxidation include pH and/or the presence of a catalyst.

Wet oxidations typically occur at temperatures above the normal boiling point of water (100° C.), but below the critical point (374° C.). For example, in one embodiment, wherein the oxidant is air, the treatment temperature is greater than about 120° C. In one embodiment, wherein the oxidant is air or oxygen, the treatment temperature is between about 140° C. and about 330° C. In another embodiment wherein the oxidant is air or oxygen, the treatment temperature is between about 225° C. and about 275° C. In one embodiment, wherein the wet oxidation is a WAO, the treatment temperature of is between 150° C. and about 330° C., whereas the total pressure is between 1 MPa (~150 psi) and 22 MPa (~3200 psi). In general, the pressure of the system may be selected and/or maintained to provide a specific concentration of oxidant and/or to prevent excessive evaporation. In one embodiment, the partial pressure of oxygen is between 0.15 MPa (~22 psi) and 11 MPa (~1600 psi). In another embodiment, the partial pressure of oxygen is between 0.3 MPa (~50 psi) and 1.4 MPa (~200 psi). In one embodiment, wherein an air stream is used, the total pressure is between about 2 MPa (~290 psi) and about 22 MPa (~3200 psi). In one embodiment, the oxidant may be added at a concentration corresponding to 30% to 250% of the chemical oxygen demand (COD) of the biomass. In one embodiment, the oxidant may be added at a concentration corresponding to about 150% of the COD. In general, the duration of the wet oxidation may include any suitable time period. In one embodiment, wherein the oxidant is air or oxygen and the treatment temperature is between about 140° C. about 330° C., the reaction time is between about 10 minutes and 2 hours. In one embodiment, wherein ozone is the oxidant and the treatment temperature is between 0° C. to about 60° C., the treatment duration is between about 5 and about 30 minutes. In general, the pH may vary depending upon the biomass and/or whether the biomass has been pretreated. In one embodiment, the pH is within the range from about 2 to about 12. In one embodiment, the pH is adjusted by adding acid or alkali to the biomass stream prior to or during the wet oxidation step. In one embodiment a catalyst is added to the wet oxidation. In fact, catalytic wet air oxidation (CWAO), wherein the stream to be oxidized is passed over a catalyst at elevated temperatures and pressures, is believed to be particularly cost-effective for streams having a COD greater than 10,000 mg/L. Although the process and/or equipment may be simpler if the temperature within the reactor is between about 100° C. and about 374° C., while the pressure is below about 22 MPa (e.g., such that there is a liquid component), in other embodiments, the temperature and/or pressure is higher. For example, in one embodiment, the temperature and/or pressure is above the mixture's thermodynamic critical point such that the wet oxidation is a supercritical water oxidation (SCWO).

The level of wet oxidation achieved may be described as either partial oxidation or complete oxidation, and may be generally assessed by the substances formed/remaining. For example, the wet oxidation of dissolved or suspended organic substances typically converts high molecular weight compounds to lower molecular weight compounds (e.g., via various intermediates), with a complete oxidation generally associated with carbon dioxide and water as the final products. Similarly, a complete oxidation of inorganic components, typically converts multivalent metallic cations to the highest oxidation state possible, and converts all sulfur containing compounds to sulfates.

While the wet oxidation 10 illustrated in FIG. 1 may be run to completion (i.e., producing primarily $CO_2$ and $H_2O$), it is also advantageous to select the wet oxidation conditions to produce small chain (e.g., C4 or lower), saturated carboxylic acids and/or the corresponding salts. In fact, it has been reported that low molecular weight carboxylic acids (e.g., R—$CO_2H$), and acetic acid ($CH_3CO_2H$) in particular, are quite resistant to oxidation, and thus tend to accumulate at the latter stages of wet air oxidation. For example, the wet oxidation effluent may include acetic acid, formic acid, and/or oxalic acid. In one embodiment, the wet oxidation conditions are selected to produce primarily acetic acid and/or acetate ($CH_3CO_2^-$), or at least to maximize the yield of acetic acid and/or acetate ($C_2H_3O_2^-$). In general, even when the wet oxidation conditions are selected to maximize the production of acetic acid/acetate, some $CO_2$ may be produced. Advantageously, wet oxidation products/by-products such as acetate, acetic acid, and/or $CO_2$ may be converted to ethanol.

The wet oxidation may be conducted in batch or continuous mode. Conducting the wet oxidation in continuous mode is generally advantageous in large scale applications. One example of a known commercially available unit for conducting a continuous mode wet oxidation 10 is a Zimpro® wet oxidation unit available from Siemens. In Zimpro® wet oxidation systems, the stream fed to wet oxidation is typically pressurized and then fed to a heat exchanger wherein the input stream is preheated by indirect heat exchange before entering the wet oxidation reactor, wherein it is mixed and reacted with the oxidant. The organic material in the stream is oxidized at the predetermined temperature and a pressure that is controlled to maintain a liquid phase. The oxidized stream and off-gases pass from the reactor to the heat exchanger, where it is cooled.

Figure 2:
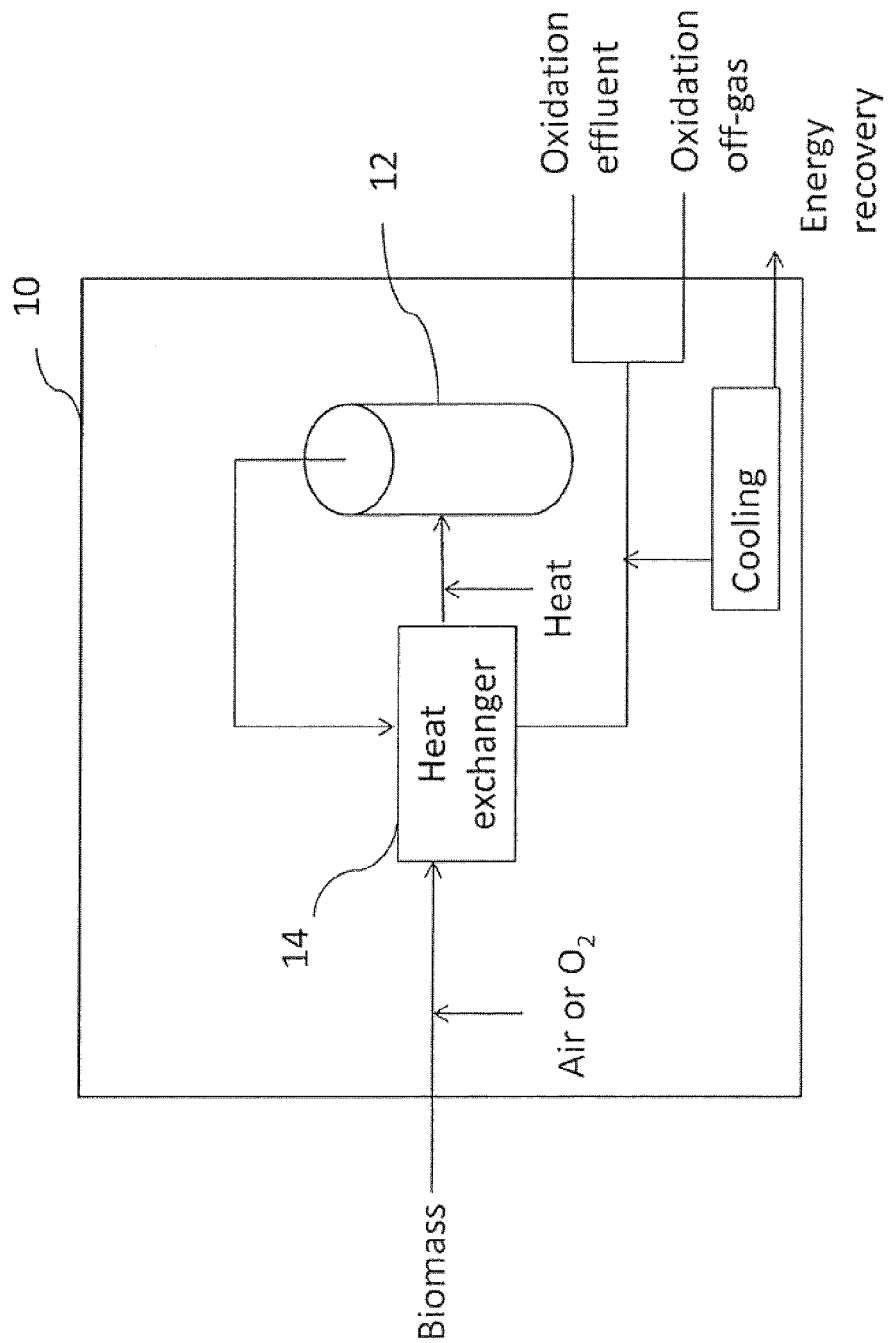
FIG. 2 is a schematic diagram showing an embodiment of a wet oxidation.

Referring to FIG. 2, there is shown a schematic diagram of a wet oxidation unit suitable for use in the wet oxidation 10. A stream including biomass (e.g., an aqueous slurry) enters the wet oxidation via a feed pump (not shown), which may also bring the biomass strewn up to the system pressure. Air and/or oxygen is introduced to the biomass stream via a compressor. To initiate the wet oxidation (e.g., for a cold start), heat may added to the biomass prior to entering the reactor 12 and/or to biomass resident within the reactor 12 in an amount that meets or exceeds the energy required to start the wet oxidation. In this embodiment, the reactor 12 is a bubble column reactor. Once the wet oxidation reaction has started, the reaction may generate heat that may help to maintain the reactor temperature (e.g., it may even be self-sustaining or may generate excess heat). In one embodiment, the heat introduced for the cold start includes direct steam injection into the reactor 12. The residence time of the heated biomass within the reactor 12 may be selected in dependence upon the oxidant, the reactor pressure, the reactor temperature, and the desired degree of oxidation. The hot, pressurized, and treated stream exits from the top of the reactor 12, and is then fed to the heat exchanger 14, while new biomass enters the reactor 12. In the heat exchanger, at least a portion of the heat from the treated stream is transferred to the biomass to be fed to the reactor 12. File effluent from the reactor 12 may then be cooled by cooling water (e.g., which may produce steam for energy recovery). The cooled effluent is then fed to a separator that separates the oxidation off-gas (e.g., which may include carbon dioxide ($CO_2$), nitrogen ($N_2$), and/or steam) from the oxidation effluent (e.g., which is typically aqueous and may include carboxylic acids, such as acetic acid and formic acid). As is known in the art, the wet oxidation unit may also include one or more pressure control valves (not shown), which may also be used for temperature control. In addition, the wet oxidation unit may include a mechanical stirrer and/or other agitator. In One embodiment, adequate mixing is achieved by bubbling the oxidant into a lower section of the vertical reactor. Notably, the system illustrated in FIG. 2 is particularly useful when the stream fed to the wet oxidation is highly alkaline, since the $CO_2$ present/produced in the system may tend to be present in solution as carbonate.

Figure 3:
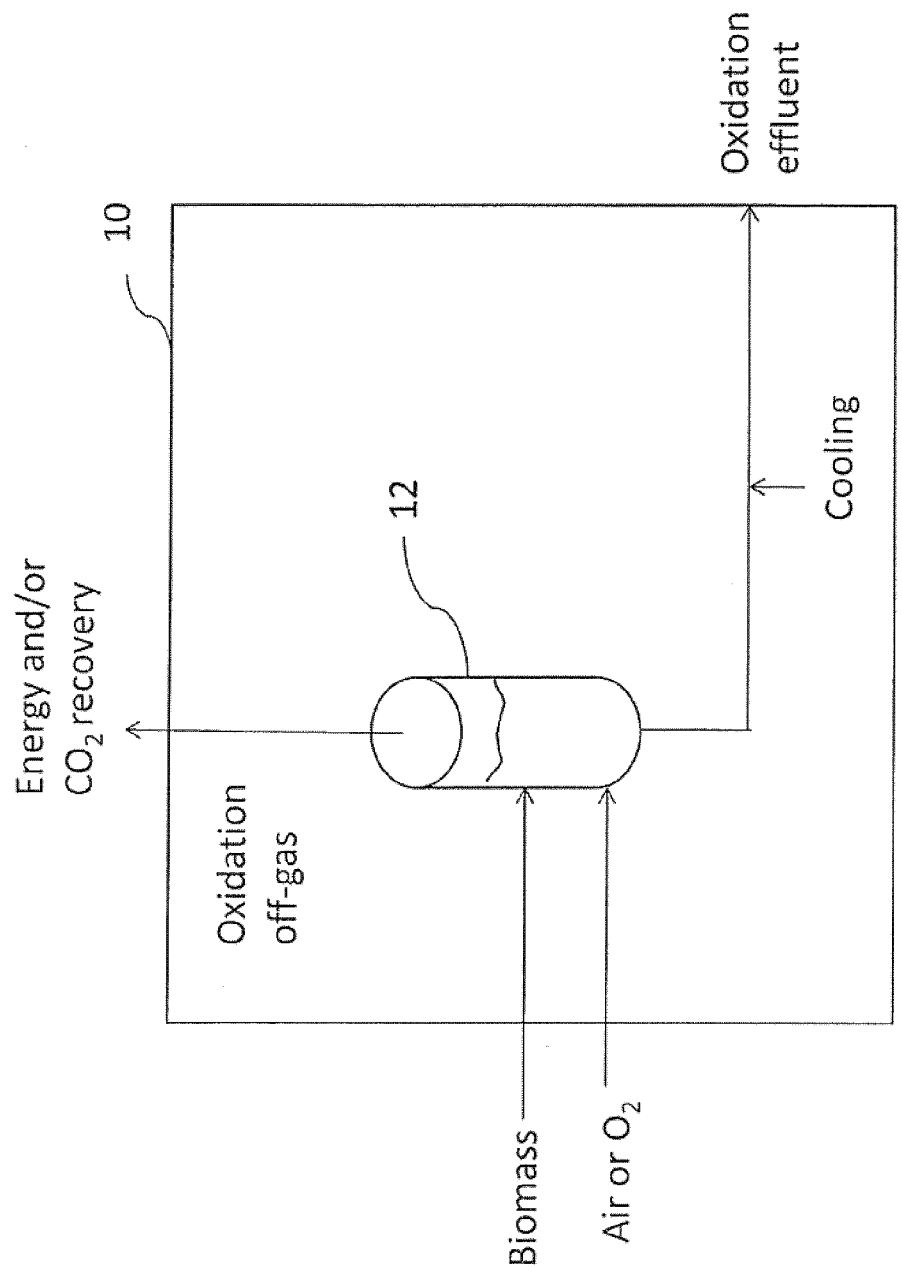
FIG. 3 is a schematic diagram showing an embodiment of a wet oxidation.

Referring to FIG. 3, there is shown a schematic diagram of another embodiment of a wet oxidation unit suitable for use in the wet oxidation 10. In this embodiment, the stream of biomass enters the wet oxidation via a feed pump or conveyor (not shown). Both the biomass and oxidant (e.g., air and/or oxygen) introduced to reactor 12. In addition, water may be introduced to the reactor 12 to provide the required water and/or to maintain the liquid level. For a cold start, heat is introduced into the reactor 12 in an amount that meets or exceeds the energy required for the wet oxidation. Once the wet oxidation reaction has started, heat may be produced and may be used to maintain the reactor temperature (e.g., either directly and/or indirectly via a heat exchanger). The heat introduced for the cold start may include direct steam injection or one or more heaters. The biomass resides within the reactor for a predetermined duration, which is selected in dependence upon the oxidant, the concentration of the oxidant, the reactor temperature, and/or the desired degree of oxidation. The energy generated by the wet oxidation may be absorbed by evaporation of water in the reactor. The water vapour and noncondensible gases exit the reactor from the top. Since a relatively large amount of steam may be generated during the wet oxidation, energy may be recovered from the vented stream. For example, in one embodiment, the vented steam is fed to a heat exchanger (not shown), wherein the vented steam is heat exchanged against boiler feedwater to generate clean steam that may be used elsewhere in the process. In general, the generated steam (e.g., vented or clean) may be fed to a power generator. Oxidation effluent may exit from the bottom and/or top of the reactor 12. For example, in one embodiment, any ash and/or other solids that accumulate in the reactor is continuously discharged as a small blowdown stream from the bottom of the reactor with some effluent. Alternatively, the reactor contents (e.g., including any ash) may be periodically purged and/or filtered to provide the oxidation effluent. In another embodiment, at least part of the oxidation effluent exits with the off-gases/steam at the top of the reactor 12. As is known in the art, the wet oxidation unit may also include one or more pressure control valves (not shown), which may also be used for temperature control. In addition, the wet oxidation unit may include a mechanical stirrer and/or other agitator. In one embodiment, adequate mixing is achieved by bubbling the oxidant into a lower section of the vertical reactor. In one embodiment, the wet oxidation is conducted via multiple stages (e.g., in a single reactor or in more than one reactor).

As described above, wet oxidation is an exothermal reaction, and thus the process may generate recoverable heat. The energy generated during wet oxidation may be used to maintain the wet oxidation reaction temperature, may be used for heat integration within the system (e.g., in producing and/or recovering the biofuel), and/or may be used to generate electricity. In one embodiment, steam resulting from the wet oxidation (e.g., directly or indirectly) is fed to any stage of the process in which heat input is required. In one embodiment, steam resulting from the wet oxidation is introduced to a step within the process under high or low pressure. In one embodiment, steam resulting from the wet oxidation is fed to a heat exchanger. For example, in one embodiment, heat is transferred from the steam resulting from the wet oxidation and a heat transfer fluid. In one embodiment, the steam is fed to a heat exchanger and condensed. The heat recovered from the heat exchanger may be used to supply heat to the wet oxidation.

In one embodiment, the wet oxidation reactor is designed to optimize energy recovery, as shown for example in U.S. Pat. No. 4,100,730. In one embodiment, the steam and/or noncondensible gases are fed to a turbo-generator wherein the exhaust gases pass into a gas expander, and are used to drive a generator (e.g., to generate electricity) and/or used to drive an air compressor (e.g., used to provide the oxidant to the wet oxidation).

In the embodiments illustrated in FIGS. 2 and 3, the wet oxidation reactor is a bubble column reactor. In other embodiments, the wet oxidation reactor is a vertical tube reactor. In one embodiment, the wet oxidation reactor is a gravity pressure vessel.

In one embodiment, wherein the biomass comprises lignocellulosic feedstock, the wet oxidation conditions are sufficient to convert at least a portion of the lignin, cellulose, and/or hemicellulose to acetic acid, acetate, and/or $CO_2$.

Alcohol Conversion

Referring again to FIG. 1, at least one of the products/by-products of the wet oxidation 10 is fed to an alcohol conversion 20. The alcohol conversion 20, converts each of the preselected products/by-products from the wet oxidation into an alcohol. In one embodiment, the alcohol is a transportation fuel (e.g., bioethanol) or fuel intermediate.

Figure 4:
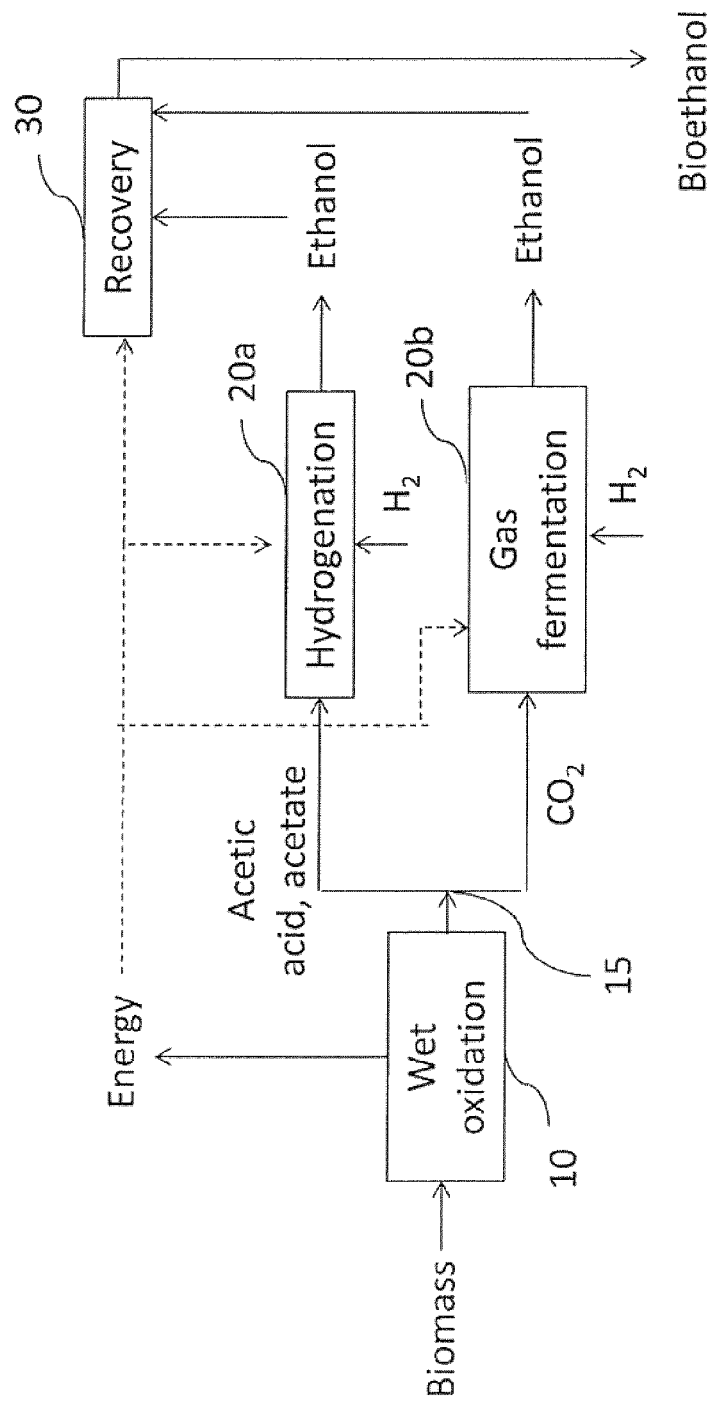
FIG. 4 is a flow diagram of a method in accordance with one embodiment of the invention, wherein the conversion to ethanol has two stages.

In one embodiment, the alcohol conversion 20 includes a conversion of acetic acid and/or acetate to ethanol. In another embodiment, the alcohol conversion includes a conversion of $CO_2$ to ethanol and/or acetic acid/acetate. In yet another embodiment, the alcohol conversion includes a first conversion that converts acetic acid and/or acetate to ethanol and a second conversion that converts $CO_2$ to ethanol and/or to acetic acid/acetate. For example, referring to FIG. 4, there is shown an embodiment of the invention wherein the alcohol conversion 20 includes a first conversion 20a for converting acetic acid and/or acetate to ethanol and a second conversion 20b for converting $CO_2$ to ethanol.

In each section 20a/20b of the alcohol conversion 20, the preselected product/by-product may be concentrated and/or purified before being fed to the corresponding reactor.

For example, if the preselected product/by-product is $CO_2$, then the $CO_2$ in the oxidation off-gas may be collected, concentrated, and/or purified. Some non-limiting examples of known $CO_2$ collection methods from a gaseous mixture include using a liquid absorbent, using a solid sorbent, membrane separation, compression and/or liquefaction. After capturing the $CO_2$, the liquid absorbent or solid sorbent is regenerated to release the carbon dioxide. The liquid absorbent or solid sorbent may subsequently be used to capture more $CO_2$. Some examples of solid sorbent include minerals, zeolites and activated carbon.

If the preselected product/by-product is acetic acid and/or acetate, then the acetic acid and/or acetate in the aqueous effluent may be isolated, concentrated, and/or purified. For example, in the reactor 12 shown in FIG. 2, the acetic acid/acetate may be recovered from the oxidation effluent or oxidation off-gas, whereas in the reactor 12 shown in FIG. 3, the acetic acid/acetate may be recovered from the oxidation effluent exiting from the bottom of the reactor and/or from the effluent corresponding to the oxidation off-gas/ steam stream (e.g., after condensation). Some non-limiting examples of known acetic acid/acetate recovery methods include extraction (e.g., liquid-liquid) followed by distillation, or salt formation and evaporation. Although acetic acid/acetate also may be recovered from aqueous solutions by conventional distillation, this may require a distillation tower with a high number of theoretical stages and/or high reflux ratio as a result of the closeness of their boiling points and the deviation from ideal solution behavior. In addition, since acetic acid boils at 118° C., whereas water boils at 100° C., conventional distillation of weak acetic acid solutions may be relatively expensive since all of the water (e.g., and ethanol if present) must be distilled away to recover the acetic acid. Another approach that may be used to separate the acetic acid/acetate from water is to use an azeotropic distillation, wherein an additional component is added to the column to improve the relative volatility of the separation and/or reduce the separation requirements. For example, when separating acetic acid and water some examples of compounds that may be added are ethyl acetate, butyl acetate, ethyl n-valerate, 4-methyl-2-pentanone. Yet another approach that may be used to separate acetic acid/acetate from water is to use an extractive distillation. In extractive distillation, the distillation may be conducted in the presence of an added liquid, which is generally non-volatile, has a high boiling point, and is miscible with the components, but does not form an azeotropic mixture. The added liquid interacts differently with the components of the mixture thereby causing their relative volatilities to change. For example, extractive distillation of acetic acid is discussed in U.S. Pat. No. 5,167,774. Optionally, the acetic acid may be concentrated prior to distillation. For example, in one embodiment the acetic acid is extracted from the wet oxidation effluent (e.g., which has been optionally treated and/or filtered to remove unwanted components) with an organic solvent/mixture (e.g., n-butyl acetate and n-butanol), is subjected to a neutralization with aqueous ammonia (e.g. to produce an organic phase corresponding to the organic solvent/mixture and an ammonium acetate containing aqueous phase), is subject to a thermal treatment that decomposes the ammonium acetate to produce acetic acid/ acetate, which may then be distilled (e.g. as described in U.S. Pat. No. 4,100,189 to Mercier).

In one embodiment, the acetic acid, acetate, and/or $CO_2$ are not subject to a recovery step before being fed to the corresponding reactor. For example, in one embodiment, the streams containing acetic acid, acetate, and/or $CO_2$ are subject to one or more steps that remove at least a portion of the undesirable components, or are fed directly to a step of the alcohol conversion.

$CO_2$ Conversion to Alcohol

In one embodiment, the section that is used to convert $CO_2$ to ethanol includes a gas fermentation unit. In One embodiment, the gas fermentation unit includes a fermentation reactor into which hydrogen ($H_2$) and $CO_2$ are fed. The $CO_2$ and/or CO (e.g., the latter of which may be present in the off-gas or which may be formed upon the addition of $H_2$) functions as a substrate for the biologic conversion to ethanol, which utilizes microorganisms or other biocatalysts.

In one embodiment, the fermentation reactor is a deep tank bioreactor, which is a reactor generally having a depth of greater than 10 meters. The deep tank reactor may be stirred to facilitate contact between the gases and the liquid nutrient broth. In one embodiment, the gases are introduced at the lower end of the reactor and allowed to bubble through the liquid broth. In another embodiment, the gases are introduced along with the liquid broth (e.g., together with a broth re-circulation stream). In one embodiment, mechanical pumping is utilized to facilitate liquid flow and mass transfer. In another embodiment, the fermentation reactor is another type of reactor, such as a gas lift reactor, wherein the broth is agitated through the use of gas nozzles.

In one embodiment, the fermentation reactor employs cell recycle in order to replenish the concentration of microorganisms therein. For example, in one embodiment, a liquid stream containing cells is withdrawn from the fermentation reactor and sent to a solids-liquid separation (e.g., a microfiltration system or cell-retention system) to separate cells from the effluent stream. The separated cells are returned to the fermentation reactor and a substantially cell-free stream resulting from the separation may be sent to alcohol recovery (e.g., for ethanol, alcohol recovery may include distillation).

In one embodiment, the microorganisms or other biocatalysts used in the fermentation reactor include a hydrogen oxidizing chemoautotroph. In one embodiment, the microorganisms used include any bacterium in a genus selected from *Acetogenium, Acetobacterium, Acetoanaerobium, Butyribacterium* and *Clostridium* that are capable of the bioconversion. In one embodiment, the microorganism is from the genus *Clostridium*. Without being limiting, a particularly suitable microorganism for producing ethanol from $CO_2$ and $H_2$ is *Clostridium ljungdahlii*. For example, *Clostridium lfungdahlii* is believed to produce ethanol by the following pathway reactions:

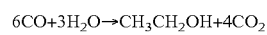

In one embodiment, the gas fermentation is used to produce ethanol directly from the $CO_2$ collected from the wet oxidation, using bacteria from the genus *Clostridium*. In addition to ethanol, *Clostridium* bacteria may produce significant amounts of acetic acid and/or acetate, depending on the process conditions, in addition to ethanol. For example, *Clostridium* species is believed to produce acetic acid by the following reaction mechanism:

In fact, *Clostridium* bacteria may have a natural tendency to form acetic acid in greater amounts than ethanol. Accordingly, the fermentation conditions typically need to be adjusted (e.g., by nutrient limitation or by providing excess $H_2$ or CO) to achieve the desired ethanol productivity.

Figure 5:
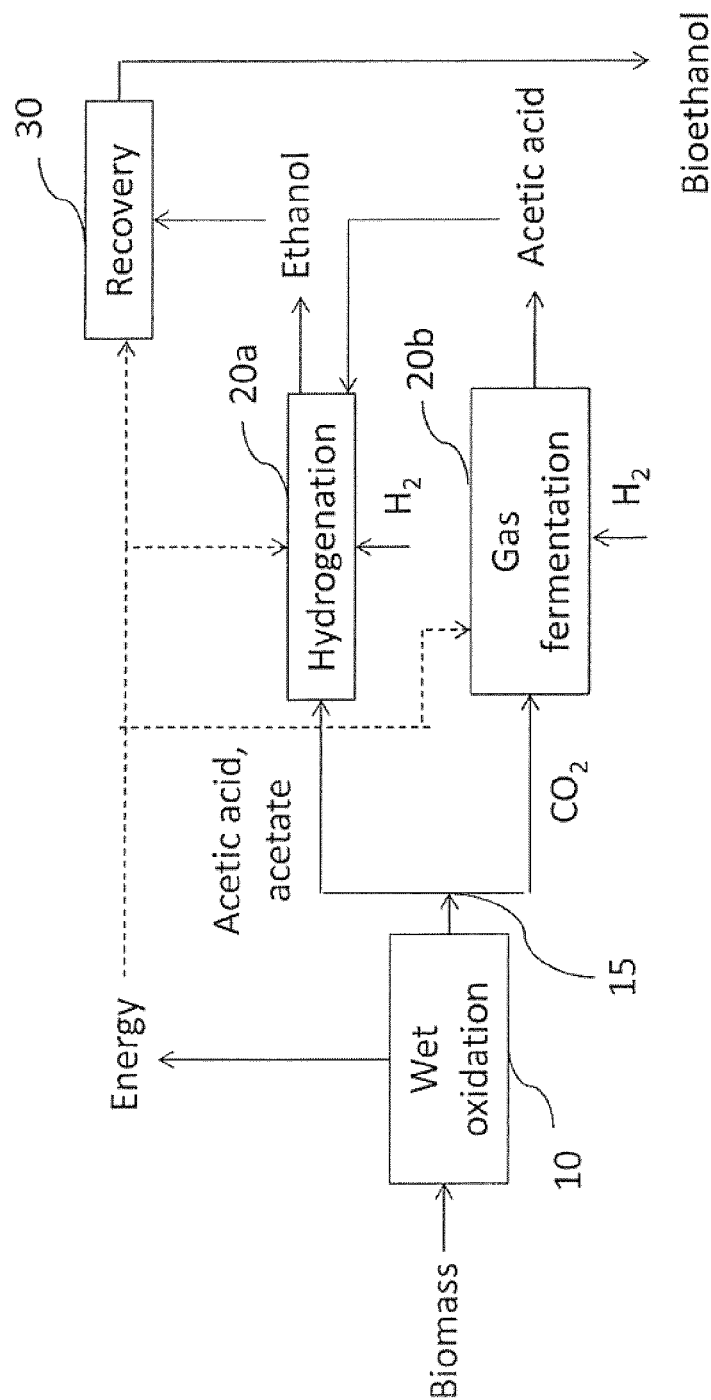
FIG. 5 is a flow diagram of a method in accordance with one embodiment of the invention, wherein the conversion to ethanol has two stages.

In one embodiment, the gas fermentation conditions are selected to maximize the production of acetic acid/acetate from $CO_2$. One fermentation parameter that may be selected to increase the production of acetic acid is pH. For example, at pH values above about 5 *Clostridium* species may produce more acetic acid/acetate than ethanol, whereas at pH values above about 3.8 and below about 5 *Clostridium* species may produce more ethanol. The acetic acid and/or acetate may then be fed to a section of the alcohol conversion 20 used to convert acetic acid/acetate to ethanol. For example, referring to FIG. 5, there is shown an embodiment of the invention wherein acetic acid/acetate formed in the second stage 20b of the alcohol conversion 20 is fed to the first stage 20a of the alcohol conversion 20. Advantageously, this embodiment exploits the natural tendency of *Clostridium* bacteria to produce acetic acid, and provides more acetic acid/acetate for the acetic acid/acetate hydrogenation reaction, thus producing more alcohol. In particular, more alcohol may be produced because the gas fermentation 20b may provide a larger yield of acetic acid than alcohol for a given amount of $CO_2$ fed therein. Further advantageously, the additional ethanol is produced from an off-gas of the process.

Acetic Acid/Acetate Conversion to Alcohol

In one embodiment, the conversion of acetic acid and/or acetate to ethanol includes hydrogenating the acetic acid and/or acetate.

In one embodiment, a hydrogenation reactor is used to hydrogenate acetic acid to ethanol in a single hydrogenation step. For example, in one embodiment the process includes a gas phase hydrogenation wherein acetic acid is catalytically reduced to ethanol in a one-step reduction. In another embodiment, the hydrogenation of acetic acid to ethanol is provided via one or more intermediates.

Theoretically, acetic acid may be reduced to ethanol according to the following stoichiometry:

$$CH_3COOH + 2H_2 \rightarrow CH_3CH_2OH + H_2O$$

However, during the catalytic hydrogenation of acetic acid, there may be other reactions that produce by-products and/or intermediates. For example, one side reaction includes an equilibrium reaction between acetic acid/ethanol and ethyl acetate/water:

$$CH_3COOH + CH_3CH_2OH \leftrightharpoons CH_3COOCH_2CH_3 + H_2O$$

In one embodiment, the hydrogenation of acetic acid may favour the production of ethyl acetate over ethanol (e.g., using some platinum/copper or palladium/cobalt catalysts). The ethyl acetate is then hydrogenated to ethanol according to:

$$CH_3COOCH_2CH_3 + 2H_2 \rightarrow 2CH_3CH_2OH$$

In one embodiment, the acetic acid is converted to ethanol using one of the catalytic hydrogenation reactions known in the art. The hydrogenation reaction may be carried out in either the liquid phase or vapor phase.

For example, in one embodiment, the hydrogen used to hydrogenate the acetic acid and/or ethyl acetate is provided by a hydrogen production unit (e.g., which includes a gas input for receiving a stream of pure hydrogen). In one embodiment, acetic acid, ethyl acetate, or a mixture thereof, is introduced into a vaporizer, together with the stream of pure $H_2$. The resulting gaseous mixture, which may have a temperature between 100° C. and 300° C., is then fed to a reactor that contains the catalyst used in the hydrogenation of the carboxylic acid or ester. Once the hydrogenation process has progressed to a certain point, a crude alcohol product may be withdrawn (e.g., continuously). Advantageously, energy (e.g., steam) generated during the wet oxidation may be used to provide energy to the hydrogenation reactor and/or the hydrogen production unit.

In one embodiment, the hydrogenation reactor includes a fixed bed reactor or a fluidized bed reactor. In one embodiment, the catalyst is employed in a fixed bed reactor, e.g., in the shape of a pipe or tube, where the reactants, typically in the vapor form, are passed over or through the catalyst. In one embodiment, the contact time between reactants and the catalyst is between 0.1 to 100 seconds, although it may extend to several hours.

In general, the catalyst may be any catalyst known in the art that produces the conversion. For example, in one embodiment, the catalyst comprises two or more metals on a support. The metals may include copper, molybdenum, tin, chromium, iron, cobalt, vanadium, tungsten, palladium, platinum, rhodium, lanthanum, cerium, manganese, gold, nickel, and combinations thereof. Exemplary metal combinations include platinum/tin, platinum/cobalt, platinum/tungsten, platinum/chromium, platinum/palladium, platinum/cerium, palladium/tin, palladium/tin, palladium/cobalt, rhodium/tin, cobalt/tungsten, cobalt/chromium, cobalt/zinc, cobalt/tin, copper/palladium, copper/zinc, nickel/palladium, or gold/palladium. The supports may include silicaceous supports. For example, in one embodiment, the catalyst is a silica-supported platinum-tin catalyst wherein the molar ratio of platinum to tin varies from 0.4:0.6 to 0.6:0.4, or is 0.5:0.5. In one embodiment, the hydrogenation catalyst may comprise at least three metals.

In one embodiment, the acetic acid/acetate and/or acetic acid ester is converted to ethanol using one of the hydrogenation processes and/or catalysts described in any of U.S. Pat. Publ. Nos. 2013/0345478, 2014/0128642, 2014/0142351, and 2015/0133701, or U.S. Pat. Nos. 7,863,489, 8,552,225, and 8,772,553.

In another embodiment, ethanol may be produced by esterifying the acetic acid with an olefin, having at least 4 carbon atoms (e.g., 1-butene, 2-butene, isobutene, 1-amylene, 2-amylene, 3-amylene, iso-amylene, 1-hexene, 2-hexene, 3-hexene, etc). The resulting ester may then be hydrogenated according to:

$$CH_3COOR + 2H_2 \rightarrow CH_3CH_2OH + ROH$$

to yield ethanol and a higher alcohol having at least 4 carbon atoms. For example, in one embodiment, the acetic acid is converted to ethanol using a process discussed in U.S. Pat. No. 4,421,939. In another embodiment, the acetic acid is converted to ethanol using a process described in U.S. Pat. No. 8,232,440.

In yet another embodiment, the acetic acid and/or acetate is converted to ethanol using other esterification and hydrogenation reactions. For example, in one embodiment the acetic acid is converted to an ester of acetic acid using a processes described in any of U.S. Pat. Nos. 6,509,180, 6,927,048, and 7,351,559 followed by a hydrogenation reaction (e.g., as also described in U.S. Pat. Nos. 6,509,180, 6,927,048, and 7,351,559). For example, in one embodiment, the acetate may be acidified with carbon dioxide to produce acetic acid and calcium carbonate and esterified to an acetic acid ester for recovery. In one embodiment, the process includes forming a complex between an amine and the acetate ion, esterifying the acetic acid from the amine complex to an acetic acid ester (e.g., in the presence of an alcohol), and hydrogenating the acetic acid ester to recover the ethanol, as discussed in U.S. Pat. No. 6,927,048.

Advantageously, when the esterification includes ethanol as the alcohol, the resulting acetic acid ester is ethyl acetate, which is volatile (e.g., has a boiling point lower than water of about 77° C.) and may be distilled away from the bulk volume. The recovered ethyl acetate may then be hydrogenated as discussed above. Accordingly, the cost of the recovery process may be less than one wherein bulk volume must be distilled away from acetic acid.

In one embodiment the acetic acid formed in the wet oxidation is esterified with an alcohol, such as methyl or ethyl alcohol, to form the volatile ester, followed by a reactive distillation to push the esterification equilibria to high conversion (e.g., including the continuous removal of one or more products). As discussed above, if the ester is ethyl acetate, the most volatile component in the reaction mixture may be the ethyl acetate/water/ethanol azeotrope, which means that the bulk of the water does not need to be evaporated in order to recover the acetic acid. The ethyl acetate is then subjected to a hydrogenation reaction in which ethyl acetate is converted to ethanol (e.g., wherein one molecule of ethyl acetate produces two molecules of ethanol). The hydrogenation may be performed in either the liquid phase or the gas phase. The ethanol yield may be increased by increasing the partial pressure of hydrogen. Typical reaction conditions are 150-250° C. and 500-3000 psi depending upon the desired conversion and selectivity. The reaction can be catalyzed by any suitable hydrogenation catalysts, such as copper chromite, nickel, Raney nickel, ruthenium, and platinum. A copper chromite, nickel, or Raney nickel catalyst is preferred for the hydrogenation since these catalysts are not poisoned by water. In one embodiment, the hydrogenation is in the liquid phase and uses an alcohol such as ethanol as a solvent. In another embodiment, the hydrogenation is in the gas phase. In this embodiment, the ethyl acetate feed is vaporized and led to the hydrogenation reactor with an excess of hydrogen. After passing through the bed, the vapors are cooled and flashed into a low pressure knockout drum. The hydrogen rich vapor phase may be recycled back to the reactor. The liquid phase is distilled to remove residual water and unreacted ethyl acetate. Another distillation column may be used for a final polishing step, depending upon the nature and quantities of side products from the esterification and hydrogenation units. For example, in one embodiment, the hydrogenation of ethyl acetate includes one of the processes discussed in US Pat. Publ.: 2013/0345478, 2014/0128642, and 2014/0142351.

Advantageously, when the ester is ethyl acetate, it avoids the introduction of a second compound into the process that may need to be purified away from the product stream.

Further advantageously, the source of hydrogen for the hydrogenation reaction may be from a hydrogen production unit that also provides a $H_2$ feed to the gas fermentation. In one embodiment, the hydrogen production unit includes a steam reformer for the steam reforming of methane (e.g., typically fossil derived, but may be biogenic).

In yet another embodiment, the esterification produces butyl acetate. For example, butyl acetates may be produced by the Fischer esterification of butanol (or its isomer) and acetic acid in the presence of catalytic sulfuric acid under reflux conditions. Butyl acetate, which has a boiling point of about 126° C., may be recovered using any methods known in the art (e.g., solvent extraction, etc).

In one embodiment, esters of acetic acid are subject to a hydrogenation reaction described in any of U.S. Pat. Nos. 2,782,243, 4,113,662, 4,454,358, and 4,497,967.

In both the direct hydrogenation route and the esterification and hydrogenation route, the acetic acid and/or acetate in the oxidation effluent may be isolated, concentrated, and/or purified first. For example, as discussed above, some non-limiting examples of known acetic acid and/or acetate recovery methods include extraction followed by distillation, salt formation and evaporation, extractive distillation, and azeotropic distillation. In general, acetic acid is a weak organic acid with pKa=4.76. Accordingly, if the solution of acetic acid is near neutral pH (i.e. pH=7.0), the acetic acid will largely be in the form of an acetate salt. Accordingly, acetic acid may be recovered by salt formation and evaporation. In addition, acetic acid has a higher boiling point than water, so that the acetic acid solution may be fed to a distillation column to distill the water away from the acetic acid. Advantageously, converting the acetic acid to ethanol using a process described in U.S. Pat. Nos. 6,509,180 and/or 6,927,048, or modified therefrom, may reduce the recovery costs by obviating the separate recovery of acetic acid (e.g., which as described above, may use an energy intensive distillation). Alternatively and/or additionally, a more complex process may be used to recover the acetic acid, in conjunction with solvent extraction.

In yet another embodiment, the conversion of acetic acid to ethanol is accomplished using a gas fermentation. For example, in one embodiment, the acetic acid is converted to ethanol according to:

$$CH_3COOH+2H_2 \rightarrow CH_3CH_2OH+H_2O$$

using a fermentation step including, for example, *Clostridium ljungdahlii* or *Clostridium carboxydivorans*, $H_2$ and CO. For example, in one embodiment, the acetic acid is converted to ethanol using a process described in US Pat. Publ. No. 2014/0038252. Providing an acetic acid and/or acetate to alcohol conversion is particularly advantageous when coupled with a wet oxidation. In particular, since acetic acid is quite resistant to oxidation (e.g., when the wet, oxidation is run at about 250° C., many or most of the organic compounds in the biomass, except for acetic and propionic acids, may be transformed to $CO_2$) the wet oxidation effluent may be rich in acetic acid with relatively low concentrations of other organic components, thus simplifying any recovery and/or treatment process. Moreover, the recovery process may be simplified since most of the input stream is converted to acetic acid and/or $CO_2$, which are easily separated. In some cases, the wet oxidation effluent may be sufficiently clean to be used directly or with only minimal treatment (e.g., salt removal and/or filtering) in an esterification reaction that produces ethyl acetate for the hydrogenation reaction, in these instances, there may be no need to recover the acetic acid, but instead only the recovery of ethyl acetate (e.g., for which the recovery is less costly).

Further advantageously, the conversion of acetic acid to ethanol (e.g., either via gas fermentation or via hydrogenation) may use hydrogen obtained from a natural gas source (e.g., via steam reforming of natural gas). For example, in one embodiment, the hydrogen is obtained by steam reforming followed by a water gas shift reaction according to the following reactions:

$$CH_4+H_2O \rightarrow CO+3H_2$$

$$CO+H_2O \rightarrow CO_2+H_2$$

Overall: $CH_4+2H_2O \rightarrow CO_2+4H_2$

In one embodiment, the water gas shift includes at least a high temperature shift, which is a water gas shift typically conducted at a temperature of at least 275° C., typically higher than 300° C. An example of a temperature range for the high temperature shift is 300° C. to 450° C.

Using hydrogen derived from natural gas is advantageous in that it may provide high energy hydrogen at a relatively low cost (e.g., natural gas is relatively abundant, and thus inexpensive, in some regions). Although natural gas is not a renewable resource, and thus may emit greenhouse gases (GHG) when reformed, the net life-cycle GHG emission of the overall conversion of the biomass to alcohol may be reduced compared to that for gasoline and/or diesel fuels. Life-cycle GHG emission analysis is a technique that may be used to assess the environmental impacts off all stages of a fuel or fuel intermediate's life (e.g., including direct emissions, feedstock production, extracting raw material, all processing steps, distribution, etc.). Since wet oxidation is an exothermal reaction, which may produce significant heat for high chemical oxygen demand (COD) streams, net GHG emissions for a fuel or fuel intermediate produced from wet oxidation may be reduced if the wet oxidation is self-sustaining (e.g., since less energy will be required). In addition, since steam and/or electricity may be generated from the wet oxidation, this steam and/or electricity may be used within the process (e.g., heat integration) to reduce net GHG emissions of the process. For example, in one embodiment, a predetermined amount of steam and/or electricity is selected such that the GHG emissions resulting from the use of natural gas in producing $H_2$ is at least partially compensated by the greenhouse gas emission reductions provided by using the predetermined amount of steam and/or electricity generated from the wet oxidation. By this, it means that GHG emission savings from using energy from the wet oxidation by reducing energy imported from fossil sources at least partially off-sets the increase in GHG emissions resulting from the use of hydrogen made from fossil sources. GHG emissions or savings thereof can be readily determined using known methods, such as those described in WO2015/131282 (Patrick. J. Foody et al.), which is incorporated herein by reference. In one embodiment, the amount of GHG emissions resulting from the use of hydrogen from natural fossil sources is less than the amount of GHG emissions reduced by the use within the process of stream and/or electricity generated from wet oxidation. In one embodiment, the greenhouse gas emission reductions provided by using the steam and/or electricity generated from the wet oxidation contributes to a net life-cycle GHG emission of the overall conversion of the biomass to alcohol that is lower than gasoline. For example, in one embodiment, the life-cycle GHG emission is 20%, 50%, or 60% lower than that for gasoline. In addition, GHG emissions may be reduced if the carbon dioxide generated during the reforming is introduced underground in a geologic formation (i.e., carbon sequestration wherein the carbon dioxide is stored long-term to mitigate or defer its escape into the atmosphere). For example, in one embodiment, $CO_2$ from the process (e.g., from fermentation, steam methane reforming, and/or the wet oxidation) is collected and put underground. Advantageously, this GHG reduction is provided even when the relatively low cost of natural gas is exploited.

Since certain embodiment may significantly reduce life cycle GHG emissions relative to a gasoline baseline, it may allow fuel credit generation. The phrase "fuel credit" and/or "renewable fuel credit", as used herein, includes any rights, credits, revenues, offsets, greenhouse gas rights or similar rights related to carbon credits, rights to any greenhouse gas emission reductions, carbon-related credits or equivalent arising from emission reduction trading or any quantifiable benefits (including recognition, award or allocation of credits, allowances, permits or other tangible rights), whether created from or through a governmental authority, a private contract, or otherwise. For example, in one embodiment, a renewable fuel credit includes a certificate, record, serial number or guarantee, in any form, including electronic, which evidences production of a quantity (e.g., batch) of fuel meeting certain life cycle GHG emission reductions relative to a baseline set by a government authority. In one embodiment, the baseline is a gasoline baseline. Non-limiting examples of credits include Renewable identification Numbers (RINs) and Low Carbon Fuel Standard (LCFS) credits.

Under the LCFS, products for use as fuels with greater reductions in life cycle GHG emissions qualify for a greater number of credits having higher market value than fuels with lower reductions. For example, corn-based ethanol may have a life-cycle GHG emission that is at least 20% lower than gasoline, whereas cellulosic ethanol may have a life-cycle GHG emission that is at least 60% lower than gasoline. Since wet oxidation may be used produce an alcohol-based fuel from lignocellulosic feedstock and/or biomass derived from lignocellulosic feedstock, significant life-cycle GHG emission reductions may be possible.

In one embodiment, a fuel credit is generated or caused to be generated for the ethanol, or other fuel or a fuel intermediate. The fuel credit may be generated by a producer or user of the ethanol. The term "cause" or "causing", as used herein, means to arrange or bring about, either directly or indirectly, or to play a role in a series of activities through commercial arrangements such as a written agreement, verbal agreement or contract.

Alcohol Recovery

The alcohol produced in the acetic acid and or acetate conversion is recovered in one or more steps as is known in the art.

In one embodiment, the alcohol recovery includes one or more distillation columns that separate the alcohol from other components (e.g., water). The mode of operation of the distillation system depends on whether the alcohol has a lower or a higher boiling point than water. Most often, the alcohol has a lower boiling point than water, as is the case when ethanol is distilled. In embodiments where ethanol is concentrated, the column(s) in the distillation unit is typically operated in a continuous mode, although it should be understood that batch processes are also possible. Heat for the distillation process may be introduced at one or more points, either by direct steam injection or indirectly via heat exchangers. After distillation, the water remaining may be removed from the ethanol rich vapour by a molecular sieve resin, by membrane extraction, or other methods known to those of skill in the art for concentration of ethanol beyond the 95% that is typically achieved by distillation.

In embodiments wherein the effluent(s) from the alcohol conversion (e.g., which may contain acetic acid, ethanol, water, and/or excess hydrogen) is in the gas phase, it may be condensed and fed to a separator, which, in turn, forms a vapor stream and a liquid stream. For example, in one embodiment, the separator includes a flasher or a knockout pot operating at a temperature from 20° C. and 350° C. Optionally, the gaseous effluent is first passed through one or more membranes to separate any hydrogen and/or other non-condensable gases. The alcohol may then be recovered from the liquid stream.

Referring again to FIGS. 1, 4, and 5, biomass subjected to a wet oxidation is converted to alcohol (e.g., via the acetic acid/acetate and/or $CO_2$ intermediate), thus producing bioethanol (e.g., ethanol sourced from plants as opposed to front geological processes).

Ethanol produced from biomass may advantageously reduce oil dependence and/or greenhouse gas emissions. For example, ethanol produced from corn, sugar cane, and/or grasses in first generation processes has significantly increased the use of ethanol fuel worldwide. In particular, ethanol is typically considered to be a clean fuel and is commonly used in various ethanol-gasoline blends (e.g. E10, which contains 10% ethanol and 90%). The ethanol in these blends may reduce air pollution relative to unblended gasoline.

In general, first generation ethanol processes (e.g., involving the fermentation of sugars derived from corn, sugar cane, and some grasses) are relatively efficient in terms of converting the sugar or starch to ethanol. For example, corn ethanol is typically commercially produced using either a dry mill or wet mill process. Dry milling involves grinding the entire kernel into flour (e.g., meal), which is then slurried to form a mash, and then fermented using microorganisms. The resulting ethanol is transferred to distillation columns.

The stillage from the columns undergoes a process to provide distiller's dried grains and solubles (DDGS). Wet milling involves separating the kernel into its component parts (e.g., germ, fiber, protein starch) by soaking it in dilute sulfuric acid and then grinding the slurry prior to fermentation, which removes the germ, while the fiber, protein, and starch may be removed using screen, hydroclonic and centrifugal separators.

Although the unfermented residues (e.g., DDGS) in each of the dry and wet mill processes may be sold as feed, it may also be advantageous to convert the unfermented residues to ethanol using the wet oxidation 10 and alcohol conversion 20 steps discussed above. In fact, in one embodiment, the biomass fed to the wet oxidation includes stillage and/or other secondary streams from a first generation ethanol plant. Since the residues may include some cellulose, subjecting the whole stillage to the wet oxidation may produce ethanol that is considered cellulosic ethanol.

Cellulosic ethanol is attractive in that it may add value to lignocellulosic biomass that would otherwise be considered a low value byproduct of agricultural industries (e.g., corn stover, sugarcane bagasse, straw), and thus may displace more fossil fuel than through the burning, landfilling, non-utilization or co-product solutions of the agricultural waste. In addition, cellulosic ethanol production processes are beneficial in that the feedstock may be readily available in large quantities without significantly affecting food supply.

Cellulosic ethanol may, however, require a greater amount of processing relative to corn ethanol as a result of the cellulose and/or lignin present therein. For example, the cellulosic ethanol production process may include one or more pretreatment and/or hydrolysis steps in order to provide the hydrolysate containing the C5 and/or C6 sugars that are fermented to ethanol.

Advantageously, when the biomass fed to the wet oxidation 10 is sourced from a cellulosic ethanol production process, the yield of biofuel in the cellulosic ethanol production process may be increased relative to what would be obtained solely from the traditional C5/C6 sugar fermentation (e.g., for the same amount of starting material). Moreover, when the biomass fed to the wet oxidation is sourced from a secondary stream conventionally considered to be a waste or low value stream (e.g., still bottoms) of the process, the wet oxidation may treat the secondary stream and also produce intermediates for additional ethanol production. Further advantageously, since the wet oxidation may treat all secondary streams using the same conditions, one or more secondary streams may be combined in order to treat the secondary streams (e.g., and thus provide water for recycle within the process) and to produce biofuel from the combined stream.

Figure 6:
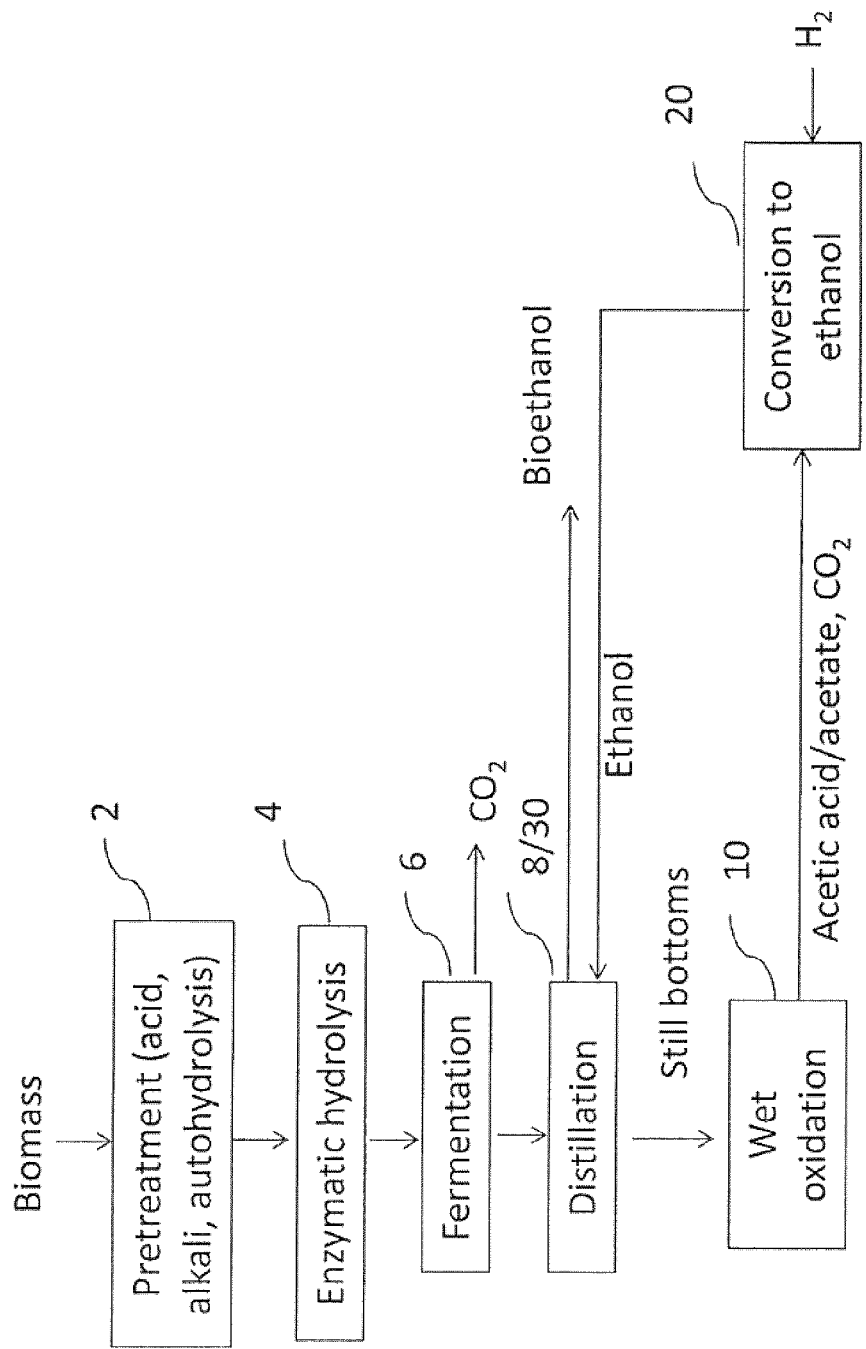
FIG. 6 is a flow diagram of a method in accordance with one embodiment of the invention, wherein the wet oxidation is integrated within a cellulosic ethanol production plant.

Referring to FIG. 6, there is shown one embodiment wherein the wet oxidation 10 and alcohol conversion 20 are integrated within a cellulosic ethanol process. The cellulosic ethanol process includes a pretreatment 2, a hydrolysis 4, a fermentation 6, and a distillation 8. In this embodiment, the biomass fed to the wet oxidation 10 corresponds to still bottoms from the distillation 8. Accordingly, the acetic acid and/or $CO_2$ and thus additional ethanol are produced from a stream typically considered a secondary stream. In addition, since acetic acid, which may be considered an inhibitor to the fermentation microorganisms used in the process, is removed from the secondary stream, the effluent water may be recycled at a greater rate without requiring further treatment (e.g. anaerobic digestion).

In this embodiment, the biomass fed to the pretreatment 2 is a lignocellulosic feedstock.

Pretreatment

In pretreatment, the feedstock is treated in one or more steps to improve the sugar yield in the hydrolysis and/or other conversion of biomass to sugar. For example, pretreatment may help to liberate the cellulose from the lignin and/or may increase the cellulose surface area. In practice, pretreatment may cause the fibrous feedstock to have a muddy texture.

In general, pretreatment may include the addition of acid, base (i.e., alkali), and/or heat. In one embodiment, the pretreatment comprises an autohydrolysis (i.e., wherein neither acid nor alkali is added). Acid pretreatment and/or autohydrolysis may hydrolyze the hemicellulose component of the feedstock to yield xylose, glucose, galactose, mannose and arabinose. Alkali pretreatment may target the lignin.

In acid pretreatment, the feedstock may be subjected to steam and a mineral acid, such as sulfuric acid, hydrochloric acid, or phosphoric acid. For example, in one embodiment the lignocellulosic feedstock is subject to a mild acid pretreatment (e.g., low concentration, high temperature) to substantially dissolve the hemicellulose component, while rendering the cellulose component more accessible to subsequent hydrolysis. Sulfuric acid is the most common mineral acid for this process.

In another embodiment, the lignocellulosic feedstock is treated with sulfurous acid, sulfur dioxide, and/or sulfonic acid. For example, in one embodiment, the pretreatment includes introducing steam and gaseous sulfur dioxide ($SO_2$) to the lignocellulosic feedstock. Subjecting the lignocellulosic feedstock to an acid pretreatment with gaseous $SO_2$ provides a relatively rapid and uniform distribution of acid, for both high and low consistency feedstocks. Advantageously, adding $SO_2$ and/or sulfurous acid during pretreatment may generate a sulfite ($SO_3^{2-}$) or bisulfate ($HSO_3^-$), which may improve the efficiency of the hydrolysis and/or fermentation, and/or may provide sulfite salts (e.g., wherein the metal is derived from the feedstock, such as $K_2SO_3$ or $KHSO_3$). Further advantageously, any sulfite salts (e.g., $K_2SO_3$, $NaHSO_3$) present in solution may be oxidized to sulfate salts by the wet oxidation, and thus may be used in fertilizers and/or soil conditioning applications.

In one embodiment, addition of acid results in a pH between about 1.0 and about 3.5, wherein the pH is measured at any stage during the time course of the pretreatment and is measured at ambient temperature.

In one embodiment, the acid pretreatment includes the addition of heat. Without being limiting, the addition of heat may result in a maximum temperature between about 60° C. and about 230° C. As will be understood by those having ordinary skill in the art, there may be a time delay in the pretreatment process before the feedstock reaches this temperature range. The above temperatures correspond to those values reached after sufficient application of heat to reach a temperature within this range. In one embodiment, the time that the feedstock is held at the maximum temperature is between about 10 seconds and about 30 minutes. In one embodiment, the feedstock is maintained at the maximum temperature for duration that is between 30 seconds and 5 minutes. Advantageously, maintaining the feedstock at the elevated temperature for less than about 5 minutes, when the acid is $SO_2$, provides an effective pretreatment with reduced costs. Alternatively, the feedstock may be maintained at the maximum temperature for a longer duration (e.g., without negative effects).

In one embodiment, a base is added after the acid pretreatment to adjust the pH of the feedstock to a suitable pH level (e.g., which is compatible with a subsequent enzymatic hydrolysis and/or fermentation). For example, in one embodiment, the pH level is determined in dependence upon the microbes used in subsequent steps. In general, many suitable enzymes and/or yeasts will be active at pH values between 4 and 7, and some may be active outside this range. In one embodiment, sufficient base is added to achieve a pH between 4 and 6. Some examples of suitable bases include ammonia ($NH_3$), ammonium hydroxide ($NH_4OH$), potassium hydroxide (KOH), sodium hydroxide (NaOH), magnesium hydroxide ($Mg(OH)_2$), calcium hydroxide ($Ca(OH)_2$), potassium carbonate ($Mg_2CO_3$), magnesium carbonate ($MgCO_3$), and the like.

In general, the addition of base to the acid-pretreated feedstock may produce one or more salts (e.g., including organic and inorganic salt). For example, in one embodiment the addition of base provides a sulfite salt (e.g., such as $(NH_4)_2SO_3$, $K_2SO_3$, $Na_2SO_3$ $CaSO_3$, $MgSO_3$, $K_H SO_3$, and the like). In one embodiment, the addition of a base provides a combination of salts (e.g., $K_2SO_3$ and $Na_2SO_3$).

In general, the alkali may be added to the acid pretreated feedstock after it is cooled, before cooling, or at points both before and after cooling.

In an alternative embodiment, the pretreatment is an alkali pretreatment. More specifically, the lignocellulosic feedstock is pretreated with base, also referred to herein as "alkali", to produce an alkali pretreated feedstock. Some examples of suitable bases include $NH_3$, $NH_4OH$, KOH, and NaOH, each of which advantageously is soluble in water. For example, in one embodiment, the lignocellulosic feedstock is treated with a dilute ammonia solution. In some embodiments, the alkali pretreatment may not hydrolyze the hemicellulose in the lignocellulosic feedstock. In some embodiments, the addition or base may alter the crystal structure of the cellulose so that it is more amenable to hydrolysis.

In one embodiment, the alkali pretreatment includes the addition of heat. Without being limiting, alkali pretreatment may be performed at a temperature between about 20° C. and about 200° C. For example, in one embodiment the maximum temperature of the pretreatment is between 100° C. and 200° C. As will be understood by those having ordinary skill in the art, there may be a time delay in the pretreatment process before the feedstock reaches this temperature range. The above temperatures correspond to those values reached after sufficient application of heat to reach a temperature within this range. In one embodiment, the time that the feedstock is held at the maximum temperature is between about 10 seconds and about 120 minutes. In one embodiment, the feedstock is maintained at the maximum temperature for duration that is between 30 seconds and 120 minutes. In one embodiment, the resulting pH is between about pH 9.5 and about pH 12.

In general, when the lignocellulosic feedstock is subject to an alkali pretreatment, an acid may be added after the base addition to adjust the pH of the feedstock to a suitable pH level (e.g., that is compatible with a subsequent enzymatic hydrolysis and/or fermentation). In one embodiment, the pH level will be determined in dependence upon the enzymes and/or microbes used in subsequent steps. For example, in one embodiment, wherein the hydrolysis is an enzymatic hydrolysis, the pH is adjusted to a pH compatible with the enzyme. In another embodiment, wherein the hydrolysis is not enzymatic, the pH is adjusted to a level compatible with the fermentation microorganisms. In one embodiment, sufficient acid is added to achieve a pH between 4 and 7. In one embodiment, sufficient acid is added to achieve a pH between 4 and 6. Some examples of suitable acids include $H_2SO_4$, $SO_2$, $H_2SO_3$, and/or $RSO_3H$, where R is an alkyl or aryl group.

In general, the acid may be added to the pretreated feedstock after it is cooled, before cooling, or at points both before and after cooling.

In one embodiment, the lignocellulosic feedstock is subject to an alkali pretreatment referred to as an Ammonia Freeze Explosion, or Ammonia Fiber Expansion ("AFEX" process). According to this process, the lignocellulosic feedstock is contacted with ammonia or ammonium hydroxide in a pressure vessel. The contact is maintained for a sufficient time to enable the ammonia or ammonium hydroxide to swell (i.e., decrystallize) the cellulose fibers. The pressure is then rapidly reduced which allows the ammonia to flash or boil and explode the cellulose fiber structure. The flashed ammonia may then be recovered according to known processes. However, this only removes a portion of the ammonia and any remaining ammonia may be neutralized with acid to produce an inorganic salt. Alternatively, the ammonia is not recovered by flashing, in which case, all or a portion of the ammonia is neutralized with acid.

In yet another embodiment, the lignocellulosic feedstock is subject to an autohydrolysis pretreatment (e.g., a hydrothermal pretreatment involving hot water or steam, where no additional chemicals such as acid or base is added, or at concentrations that do not significantly alter the pH). Since autohydrolysis may result in a slightly acidic slurry, the pH of the pretreated feedstock may be adjusted by adding a base. In general, the pH level will be determined in dependence upon the enzymes and/or yeasts used in subsequent steps.

In general, the pH adjustment may occur after the pretreated feedstock is cooled, before cooling, or at points both before and after cooling.

In general, the pretreatment (e.g., addition of acid, base, and/or heat) may disrupt the fiber structure of the lignocellulosic feedstock and/or increase its surface area to make it more accessible to the subsequent hydrolysis (e.g., acid or enzymatic). In general, the pretreatment and/or hydrolysis stages may hydrolyze a portion of the hemicellulose and/or cellulose component of the feedstock to produce sugar. However, depending on the pretreatment chemical, the pretreatment may be performed such that a certain degree of xylan hydrolysis is achieved and only a small amount of conversion of cellulose to glucose occurs. For example, in some embodiments that do not add acid or base, there may be no or limited hydrolysis of cellulose to produce glucose.

As discussed above, the feedstock is contacted with the pretreatment acid or base (e.g., as an aqueous solution) before, during, or after heating. For example, in one embodiment, a heated feedstock slurry is contacted with the pretreatment acid or base. In another embodiment, the feedstock is soaked in an aqueous solution comprising the acid or base and subsequently subjected to elevated temperature to pretreat the feedstock. In one embodiment, the treatment includes contacting the feedstock, with two or more acids or bases as required.

In one embodiment, the feedstock is contacted with steam prior to or during the pretreatment. For example, in one embodiment the feedstock is treated at elevated temperature without the addition of acid or base. In one embodiment, steam is supplied from wet oxidation, which may be carried out at elevated temperature, as discussed below. Without being limiting, the steam may be introduced to the feedstock during or prior to pretreatment and may be low, medium or high pressure steam. Various devices may be employed to introduce steam to the feedstock, such as commercially available mixing devices designed for introducing steam through spray nozzles.

Advantageously, supplying heat to the pretreatment 2 from the wet oxidation 10 can in certain embodiments allow for the elimination of a boiler that would otherwise be needed to supply such heat to pretreatment. Thus, in certain embodiments, the process is conducted without utilizing a boiler to supply heat to pretreatment. In further embodiments, the wet oxidation is the only or primary source of heat for the pretreatment. In other embodiments, reduced boiler use for pretreatment is achieved using heat from the wet oxidation. For example, greater than 50% of the heat usage in the pretreatment may be supplied by wet oxidation. In further embodiments, greater than 60%, greater than 70%, greater than 80% or greater than 90% of the heat usage in the pretreatment may be supplied by wet oxidation.

In certain embodiments, if energy from the wet oxidation 10 is provided to pretreatment 10, the amount of steam that is produced in the wet oxidation is at least the quantity of steam used in a steam heating step conducted during pretreatment.

Hydrolysis

In general, the pretreated lignocellulosic feedstock is fed to hydrolysis 4, which may be a chemical hydrolysis or an enzymatic hydrolysis. For example, in one embodiment the cellulose is hydrolyzed with a chemical, such as dilute acid. Alternatively, a more concentrated acid may be used. In these embodiments, base may be added after hydrolysis in order to adjust the pH of the solution such that it is compatible with a subsequent fermentation stage. In order for the cellulose component to be hydrolyzed, the conditions in chemical hydrolysis are typically relatively harsh and may generate compounds such as furfural and/or phenolic components, which may be inhibitory in fermentation.

In another embodiment, the pretreated lignocellulosic feedstock is fed to an enzymatic hydrolysis, wherein cellulose remaining after pretreatment is hydrolyzed to glucose. In this embodiment, which may include the addition of cellulase enzymes, the pH of the lignocellulosic feedstock may be adjusted (e.g., as part of the pretreatment and/or after pretreatment) to a value that is suitable for the enzymatic hydrolysis reaction. For example, in one embodiment acid or base is added to provide a pH in the range between about 4 to about 7, or between about 4 and about 6.5, which are optical pH ranges for many cellulases. In one embodiment, the enzymatic hydrolysis uses an alkalophilic cellulase.

The enzymatic hydrolysis of cellulose to soluble sugars can be carried out with any type of cellulase enzymes suitable for such purpose and effective at the pH, temperatures, and/or other conditions utilized, regardless of their source. Among the most widely studied, characterized and commercially produced cellulases are those obtained from fungi of the genera *Aspergillus, Humicola, Chrysosporium, Melanocarpus, Myceliopthora, Sporotrichum* and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EGV and EGVI cellulases have been isolated from *Humicola insolens* (see Lynd et al., 2002, Microbiology and Molecular Biology Reviews, 66(3):506-577 for a review or cellulase enzyme systems and Coutinho and Henrissat, 1999, "Carbohydrate-active enzymes: an integrated database approach." In Recent Advances in Carbohydrate Bioengineering, Gilbert, Davies, Henrissat and Svensson eds., The Royal Society of Chemistry, Cambridge, pp. 3-12).

In addition to CBH, EG and beta-glucosidase, there are several accessory enzymes that may aid in the enzymatic digestion of cellulose (see WO 2009/026722 (Scott), which is incorporated herein by reference and Harris et al., 2010, Biochemistry, 49:3305-3316). These include glycoside hydrolase 61 (GH61), swollenin, expansin, lucinen and cellulose-induced protein (Cip). Glucose can be enzymatically converted to the dimers gentiobiose, sophorose, laminaribiose and others by beta-glucosidase via transglycosylation reactions.

An appropriate cellulase dosage can be about 1.0 to about 40.0 Filter Paper Units (FPU or IU) per gram of cellulose, or any amount therebetween. The FPU is a standard measurement familiar to those skilled in the art and is defined and measured according to Ghose (Pure and Appl. Chem., 1987, 59:257-268). An example of a cellulase dosage is about 10 to 20 FPU per gram cellulose.

The enzyme dosage may also be measured in units of milligrams of protein per gram of cellulose. An example of a dose in these units is 2 to 20 mg protein per gram cellulose.

The conversion of cellobiose to glucose is carried out by the enzyme β-glucosidase. By the term "β-glucosidase", it is meant any enzyme that hydrolyzes the glucose dimer, cellobiose, to glucose. The activity of the β-glucosidase enzyme is defined by its activity by the Enzyme Commission as EC #3.2.1.21. The β-glucosidase enzyme may come from various sources; however, in all cases, the β-glucosidase enzyme can hydrolyze cellobiose to glucose. The β-glucosidase enzyme may be a Family 1 or Family 3 glycoside hydrolase, although other family members may be used. It is also contemplated that the β-glucosidase enzyme may be modified to include a cellulose binding domain, thereby allowing this enzyme to bind to cellulose.

As discussed above, acid or alkali may be added to the pretreated feedstock to adjust the pH of the feedstock to be compatible with enzyme hydrolysis and/or fermentation. Acid or alkali can be added to the alkali or acid pretreated feedstock, respectively, after it is cooled, before cooling, or at points both before and after cooling. When the process includes an enzymatic hydrolysis, the acid or alkali addition may be part of the pretreatment, may be part of the hydrolysis (e.g., may coincide with the cellulase enzyme addition), or may occur between the pretreatment and enzymatic hydrolysis. For example, the addition point may be upstream or downstream of the location of the enzyme addition. If the enzyme is added upstream or the acid or alkali addition point, the contact time of the enzyme at the lower pH of the pretreated feedstock would typically be minimized to avoid enzyme inactivation. The acid or alkali may be added prior to enzyme addition or simultaneously therewith.

The temperature of the slurry is adjusted so that it is within the optimum range for the activity of the cellulase enzymes. Generally, a temperature of about 45° C. to about 70° C., or about 45° C. to about 65° C., or any temperature therebetween, is suitable for most cellulase enzymes. The temperature of the slurry may be higher for some thermophilic cellulase enzymes. The duration of the enzymatic hydrolysis may be from 12 to 200 hours or any range therebetween.

If the hydrolysis 4 is enzymatic, the hydrolysis 4 and fermentation 6 may be conducted in separate vessels so that each biological reaction can occur at its respective optimal temperature. However, the hydrolysis 4 may be conducted simultaneously with fermentation 6 in a simultaneous saccharification and fermentation (SSF). SSF is typically carried out at temperatures of 35-38° C., which is a compromise between the 50° C. optimum for cellulase and the 28° C. optimum for yeast.

In one embodiment, the hydrolysis 4 provides a stream that includes aqueous sugars and may include soluble lignin and/or in soluble lignin. For example, in one embodiment, the hydrolysis provides a stream that includes both soluble sugars and insoluble solids such as lignin and/or residual cellulose.

In some embodiments, the soluble sugars are separated from the insoluble solids, wherein a stream including the soluble sugars is subject to fermentation, while the stream including the insoluble solids is subjected to a thermal process to provide heat and/or energy either within or external to the process (e.g., the burning of lignin pellets). In this case, soluble salts and/or soluble lignin may substantially remain with the aqueous stream comprising the soluble sugars. In the embodiment illustrated in FIG. 6, the stream including both the soluble sugars and the insoluble solids is fed to fermentation 6.

Fermentation

Fermentation of sugar resulting from the above pretreatment 2 and/or hydrolysis 4 may produce one or more of the fermentation products selected from an alcohol, a sugar alcohol, an organic acid and a combination thereof. In general, the fermentation may be conducted in the presence of at least one microorganism that ferments sugars to alcohols. Without being limiting, the fermentation is typically conducted at a pH between about 4.0 and about 6.0, or between about 4.5 and about 6.0.

In one embodiment, the fermentation product is an alcohol, such as ethanol or butanol. For ethanol production, the fermentation is typically carried out with a *Saccharomyces* spp. yeast. Glucose and any other hexoses present in the sugar stream may be fermented to ethanol by wild-type *Saccharomyces cerevisiae*, although genetically modified yeasts may be employed as well, as discussed below. The ethanol may then be distilled to obtain a concentrated ethanol solution. Butanol may be produced from glucose by a microorganism such as *Clostridium acetobutylicum* and then concentrated by distillation.

Xylose and arabinose that are derived from the hemicelluloses may also be fermented to ethanol by a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stiphis* (e.g., U.S. Pat. Nos. 5,789,210, 5,866,382, 6,582,944 and 7,527,927 and European Patent No. 0450430) or (b) fungal or bacterial xylose isomerase (XI) gene (e.g., U.S. Pat. Nos. 6,475,768 and 7,622,284). Examples of yeasts that have been genetically modified to ferment L-arabinose include, but are not limited to, recombinant *Saccharomyces* strains into which genes from either fungal (e.g., U.S. Pat. No. 7,527,951) or bacterial (e.g., WO 2008/041840) arabinose metabolic pathways have been inserted.

In practice, the fermentation is typically performed at or near the temperature and pH optimum of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The dose of the fermentation microorganism will depend on other factors, such as the activity of the fermentation microorganism, the desired fermentation time, the volume of the reactor and other parameters. It should be appreciated that these parameters may be adjusted as desired by one of skill in the art to achieve optimal fermentation conditions.

The fermentation may also be supplemented with additional nutrients required for the growth of the fermentation microorganism. For example, yeast extract, specific amino acids, phosphate, nitrogen sources, salts, trace elements and vitamins may be added to the hydrolyzate slurry to support their growth.

Alcohol Recovery and Residue Processing

The fermentation product is recovered, meaning that it is concentrated and/or purified from a fermented solution/slurry. A stream that contains components besides the fermentation product generated during or remaining after the recovery, is referred to herein as a "product-depleted stream". Non-limiting examples of such components include inorganic salts, unfermented sugars organic salts, soluble lignin, insoluble lignin, ash, and/or various organic compounds. As would be appreciated by those of skill in the art, such stream may comprise a certain amount of product, depending on the extent of recovery achieved.

If ethanol or butanol is the fermentation product, the recovery is often carried out by distillation, typically with further concentration by molecular sieves or membrane extraction. Another example of a recovery method is pervaporation.

The fermentation broth that is sent to distillation is a dilute alcohol solution that may contain solids such as unconverted cellulose and solid lignin, and any components added during the fermentation to support growth of the microorganisms.

Microorganisms are potentially present during the distillation depending upon whether or not they are recycled during the fermentation. In one embodiment, the broth is degassed to remove carbon dioxide and then pumped through one or more distillation columns to separate the alcohol from the other components in the broth. The mode of operation of the distillation system depends on whether the alcohol has a lower or a higher boiling point than water. Most often, the alcohol has a lower boiling point than water, as is the case when ethanol is distilled.

In those embodiments where ethanol is concentrated, the column(s) in the distillation unit is typically operated in a continuous mode, although it should be understood that batch processes are also possible. Heat for the distillation process may be introduced at one or more points either by direct steam injection or indirectly via heat exchangers. The distillation unit may contain one or more separate beer and rectifying columns, in which case dilute beer is sent to the beer column where it is partially concentrated. From the beer column, the vapour goes to a rectification column for further purification. Alternatively, a distillation column is employed that comprises an integral enriching or rectification section.

Although most of the water may be removed by distillation, a relatively small amount of water (e.g., 3.5% v/v) of water may remain since water and ethanol form an azeotrope. This mixture, which may be referred to as hydrous ethanol, can be used as a fuel alone. However, in order to mix ethanol with gasoline, the water fraction is typically removed to form anhydrous ethanol. For example, in one embodiment, the ethanol/water azeotrope is purified by adding an entraining agent (e.g., solvent such as benzene). In another embodiment, the ethanol is further purified using molecular sieves and/or other desiccants. In yet another embodiment, the ethanol is further purified using a membrane separation.

A still bottoms stream remaining after ethanol distillation is withdrawn from the bottom of one or more of the column(s) of the distillation unit. The still bottoms stream may contain acetic acid, inorganic salts, unfermented sugars, organic salts, unconverted cellulose, ash, solubilized lignin, and/or solid lignin. In general, the amount and/or presence of solids may depend upon whether the primary process stream was subject to a solid-liquid-separation after hydrolysis.

In one embodiment, the one or more distillation columns used to distill the fermentation broth are also used to recover the alcohol produced in the alcohol conversion 20. For example, in one embodiment, the effluent from the alcohol conversion 20 is fed to the distillation 8, as shown in FIG. 6 (e.g., the combined distillation is represented as 8/30). In another embodiment, a separate recovery steps are provided, as for example, illustrated in FIG. 7.

Referring to FIG. 6, the still bottoms removed from the bottom of the one or more distillation columns is fed to the wet oxidation 10. As discussed above, the wet oxidation 10 converts at least some of the organic substances (e.g., unfermented sugars, organic salts, unconverted cellulose, solubilized lignin, and/or solid lignin, if present) to at least acetic acid/acetate and/or carbon dioxide, which is then converted to an alcohol such as ethanol.

Advantageously, the wet oxidation not only provides an additional source of ethanol (e.g., increasing ethanol yield), but also treats the still bottoms, thus making disposal, water recycling within the process, and/or salt recovery, more economical. With regard to the latter, the conversion of sulfite compounds created by adding a sulfur containing acid (e.g., $SO_2$ and/or $H_2SO_3$) in any of steps 2, 4, and/or 6 to sulfate salts may simplify sulfur recovery.

For example, in one embodiment, the wet oxidation 10 provides an oxidized stream that comprises acetic acid and sulfate salts. For example, in one embodiment wherein the pretreatment includes adding $SO_2$ and/or sulfurous acid to the lignocellulosic feedstock, the wet oxidation advantageously oxidizes any sulfites to sulfates. Once the acetic acid is recovered, the effluent may then be treated to recover the salts. Alternatively, the salts may be recovered by evaporation, and the acetic acid recovered from the evaporated stream. For example, the salts may be used as a process chemical, as a salt product, or for any other use that is suitable for the salts. A "salt product" as used herein encompasses any composition comprising a salt originating from the process that is used outside the process of the present invention, typically as a vendible product. For example, salt products containing inorganic salts may be used as fertilizer to supply nutrients to soil.

Advantageously, the process described with reference to FIG. 6 integrates the wet oxidation at a point within the process that provides an efficient bolt-on process for producing additional ethanol, while also improving the yield and/or efficiency of the original process. For example, efficiency is improved since the wet oxidation combines steps of providing intermediates for ethanol production while also treating the still bottoms.

Further advantageously, the wet oxidation may provide sufficient treatment to recycle the treated water without a subsequent biological digestion. For example, although an anaerobic digestion would remove the low molecular weight organic acids (e.g., acetic acid), such acids may be removed by the alcohol conversion.

Figure 7:
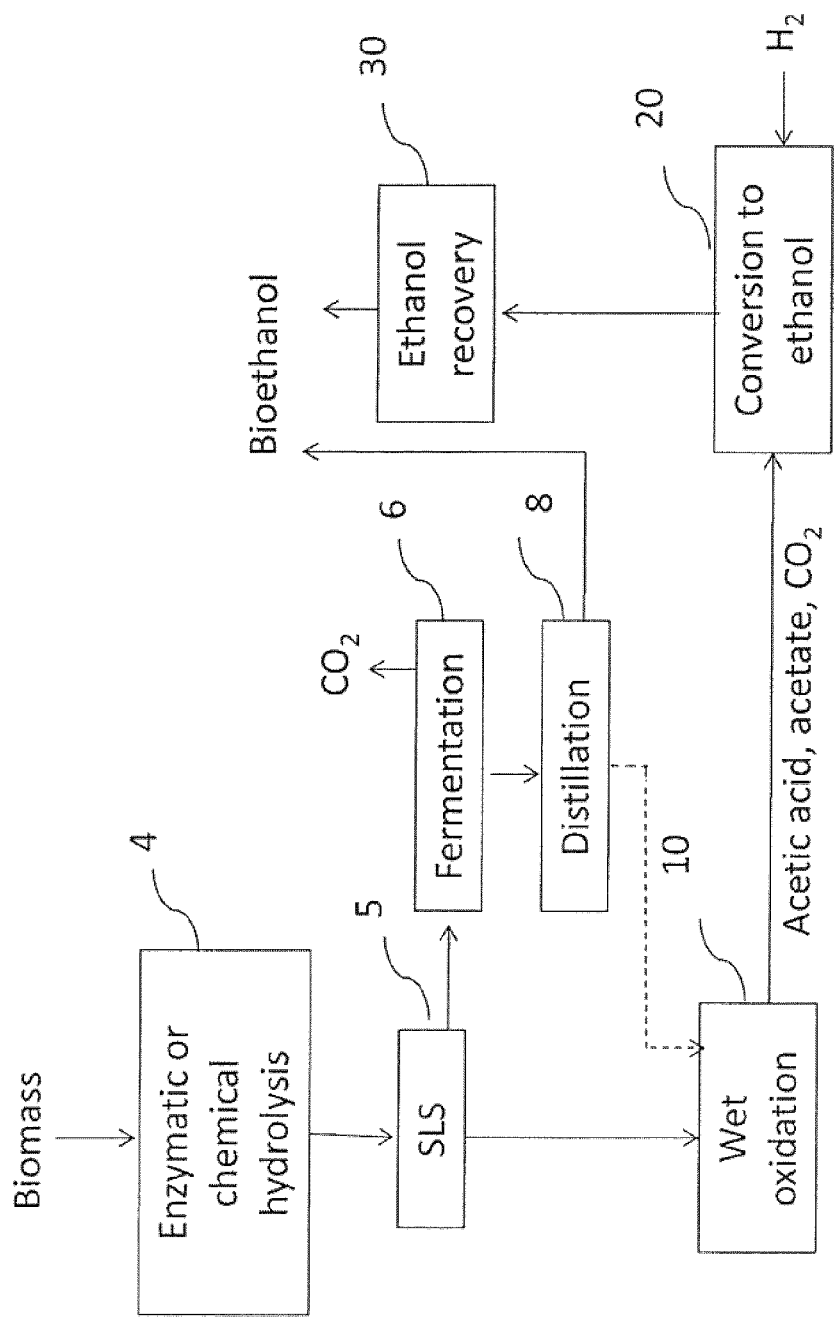
FIG. 7 is a flow diagram of a method in accordance with one embodiment of the invention, wherein the wet oxidation is integrated within a cellulosic ethanol production plant.

Referring to FIG. 7, there is shown a flow diagram of a method in accordance with another embodiment of the instant invention. In this embodiment, the wet oxidation 10 and alcohol conversion 20 are integrated within a cellulosic ethanol process wherein the effluent from the hydrolysis 4 is subjected to a solid-liquid separation (SLS) 5 prior to fermentation. In FIG. 7, the hydrolysis may be a chemical hydrolysis or an enzymatic hydrolysis. Optionally, the hydrolysis 4 is preceded by a pretreatment step (e.g., not shown, but as discussed with reference to FIG. 6). In this embodiment, the biomass fed to the wet oxidation 10 corresponds to the solid stream of the solid-liquid separation (SLS). This lignin-rich solid stream, which may be termed "lignin solids", may include ash, solid lignin, unconverted cellulose, etc. In this embodiment, the acetic acid and thus additional ethanol are produced from a stream often considered a low value stream (e.g., relative to the primary stream that produces ethanol).

Advantageously, using wet oxidation to produce ethanol from lignin may provide a relatively simple process that produces fewer pollutants (e.g., relative to combusting lignin solids or subjecting lignin solids to a gasification). In addition to converting the solid lignin to bioethanol, the wet oxidation may also include a feed from the still bottoms, and thus may provide an economic route for treating the still bottoms while increasing fuel yield and aiding to maintain the desired water level in the wet oxidation reactor. In addition, the steam generated from the wet oxidation may be integrated into any energy intensive step in the process to reduce energy import. Notably, since the solid stream produced by the SLS may have a relatively large COD it may produce a relatively large amount of steam upon wet oxidation, and thus may significantly reduce energy import into the process.

In the embodiments illustrated in FIGS. 6 and 7, the biomass streams fed to the wet oxidation include streams from cellulosic ethanol production processes that have been the subject of much discussion. For example, conventional cellulosic ethanol processes may leave between about 15 and 30 percent of the input biomass as unconverted lignin. Although, efforts have been made to use lignin as a byproduct opportunity, lignin is often simply burned for its energy value. While combusting lignin pellets is known, the cost of producing the energy product (e.g., steam/electricity) may be more expensive than alternatives without a solid fuel boiler. In accordance with one embodiment of the instant invention, lignin (e.g., solid and/or dissolved) is converted to ethanol (e.g., thus improving the overall ethanol yield) and/or heat/steam (e.g., which may be used for heat integration within the system). In fact, wet oxidation may provide the means to produce a very clean fuel from lignin, while providing a higher overall conversion efficiency of lignocellulosic biomass to ethanol in cellulosic ethanol production plants. In addition, wet oxidation treats the effluents, thus allowing water recycling.

As discussed above, in the embodiments illustrated in FIGS. 6 and 7, the biomass streams fed to the wet oxidation include lignin solids and/or still bottom streams. In accordance with another embodiment, other streams from the cellulosic ethanol production process are also fed, or alternatively fed, to the wet oxidation 10. For example, in one embodiment, streams from the pretreatment, wash water streams, and/or condensate streams are fed to the wet oxidation. In each case, the wet oxidation and alcohol conversion may advantageously increase the ethanol yield relative to the process without the wet oxidation/alcohol conversion.

In addition, integrating the wet oxidation 10 from FIG. 1 in a cellulosic ethanol production plant has various synergetic advantages. For example, when the ethanol produced from the alcohol conversion 20 is combined with the ethanol produced from the fermentation 6, more ethanol is provided to alcohol recovery 30, while the need for separate alcohol recoveries is obviated. Alternatively, the ethanol produced in the ethanol conversion 20 may be fed to the fermentation 6 (i.e., to replace fresh or recycled water that may need to be added at this stage) in order to provide a more concentrated ethanol stream to ethanol recovery 30 (e.g., a more concentrated stream may mean less water needs to be evaporated for given quantity of product).

Although the process and/or steps described with reference to FIG. 1 may be particularly useful when integrated within a conventional cellulosic ethanol production process including a fermentation, it may also be advantageous to use this process/steps as the sole source of ethanol production. For example, in one embodiment, the wet oxidation 10, ethanol conversion 20, and ethanol recovery 30 are part of a cellulosic ethanol production process that does not use a fermentation. In this embodiment, the biomass fed to the wet oxidation 10 in FIG. 1 may be raw or unprocessed lignocellulosic feedstock, such as agricultural waste.

In general, the pretreatment and/or hydrolysis steps may impact the ethanol yield and/or process costs of conventional fermentation-based second generation biofuels. For example, the enzymatic hydrolysis step is a multi-day operation that may use relatively expensive enzymes and/or enzyme mixtures. In addition, regardless of whether the hydrolysis is chemical or enzymatic, the chemicals and/or heat used in the pretreatment and/or chemical hydrolysis may be expensive. Furthermore, if an acid or base is used in the pretreatment or chemical hydrolysis, the pH of the pretreated biomass generally needs to be adjusted to a pH that is compatible with the enzymes used for hydrolysis or the microbes used for fermentation, respectively. The addition of an acid or base to adjust the pH to a suitable range increases chemical consumption, thereby adding further cost and complexity to the process. In addition, the fermentation step(s) of the C5 and/or C6 sugars may be relatively long (e.g., with a residence time in the C5 and C6 sugar fermentation reactor often between 12 hours and 48 hours) and is/are typically limited to process conditions that do not negatively impact the performance and/or viability of the yeast.

In accordance with one embodiment of the invention, the products and/or byproducts of wet oxidation (e.g., acetic acid, acetate, and/or $CO_2$) are converted to an alcohol(s) without fermenting C5 or C6 sugars. Accordingly, the pretreatment, hydrolysis, and/or fermentation steps may not be required.

Advantageously, the production of alcohols, such as ethanol, from wet oxidation is relatively simple and may be used for any biomass feedstock. For example, since lignocellulose material typically contains hemicellulose, cellulose, and/or lignin, which may vary in form/ratio depending on the source of material, the pretreatment/hydrolysis/fermentation steps are often tailored to the specific feedstock (e.g., pretreatment for woody biomass may be different than pretreatment for bagasse). Moreover, the overall process may include one or more steps for addressing specific components of the biomass (e.g., alkali pretreatment for the lignin or cellulase enzymes for hydrolyzing the cellulose). In contrast, wet oxidation processes all of the components of lignocellulose together, and may even process biomass from different sources together, thus simplifying the process.

Further advantageously, the refractory nature of acetic acid to wet oxidation and/or the final end product of $CO_2$ provides the unforeseen advantage of being able convert raw and/or processed lignocellulosic material to a specific product/intermediate in a single process step. As discussed above, fermentation-based lignocellulosic conversion processes may include various steps to address specific components of the biomass. Wet oxidation, however, may process all or most of the components of the lignocellulosic biomass with the same conditions (e.g., to produce acetic acid/acetate and/or $CO_2$). In one embodiment, the wet oxidation conditions are selected to consume a significant portion of the organic material in the biomass (e.g., to substantially reduce the COD and/or to produce a relatively high yield of acetic acid/acetate and/or $CO_2$). However, regardless of the degree of oxidation and how many organics and/or solids remain after wet oxidation, any acetic acid produced by the wet oxidation may be converted to an alcohol, as described herein.

Further advantageously, since wet oxidation is believed to oxidize contaminants, it may not be necessary for the secondary streams to be subjected to further treatment before disposal and/or recycle within the process.

Advantageously, the process/steps illustrated and discussed with reference in FIGS. 1, 4-7 may be used to produce a fuel or a fuel intermediate. For example, in one embodiment, the ethanol produced via wet oxidation and/or in the cellulosic ethanol production process is used to produce ethyl tertio-butyl ether (ETBE). Both ethanol and ETBE may be primarily used as fuels through blending into (fossil-fuel) gasoline.

Further advantageously, since wet oxidation is associated with low air emissions, and since wet oxidation may provide energy recycling/generation, providing ethanol from the organic products/by-products of a wet oxidation may provide a good alternative to, and/or may supplement, producing cellulosic ethanol via fermentation.

Of course, the above embodiments have been provided as examples only. It will be appreciated by those of ordinary skill in the art that various modifications, alternate configurations, and/or equivalents will be employed without departing from the spirit and scope of the invention. For example, although ethanol derived from biomass is particularly desirable as a transportation fuel or fuel intermediate as a result of the subsidies, tax incentives, and/or mandatory biofuel blending approved in various countries, and although ethanol fuel produced from the products/by-products of a wet oxidation may be valuable, it is also possible for the ethanol produced from the products/by-products of a wet oxidation to be used for other purposes (e.g., not as a fuel or fuel intermediate). In each case, the thermal efficiency and/or low air emissions may make ethanol production from the products/by-products of a wet oxidation desirable. Accordingly, the scope of the invention is therefore intended to be limited solely by the scope of the appended claims.

The invention claimed is:
1. A process for producing ethanol from lignocellulosic feedstock comprising:
  (i) hydrolyzing at least a portion of the hemicellulose and cellulose in the lignocellulosic feedstock to provide an aqueous mixture comprising insoluble lignin and a soluble sugar;
  (ii) fermenting the soluble sugar to provide ethanol, said fermenting comprising mixing the soluble sugar with a fermentation microorganism;
  (iii) separating the insoluble lignin from at least a portion of the soluble sugar or the ethanol;

(iv) subjecting a mixture comprising the separated insoluble lignin to a wet oxidation to produce a product comprising acetic acid, acetate, carbon dioxide, or any combination thereof;

(v) converting at least a portion of the product produced by the wet oxidation to ethanol;

(vi) recovering ethanol produced in (ii) and (v).

2. The process according to claim 1, wherein step (iii) comprises separating the insoluble lignin from at least a portion of the soluble sugar, said separating comprising conducting a solid-liquid separation on the aqueous mixture produced in (i) to produce lignin solids and a liquid comprising the soluble sugar, and wherein the mixture subjected to the wet oxidation comprises the lignin solids.

3. The process according to claim 1; wherein step (iii) comprises separating the insoluble lignin from at least a portion of the ethanol, said separating comprising distilling an aqueous mixture comprising the ethanol and the insoluble lignin, and wherein the mixture subjected to the wet oxidation comprises still bottoms from said distillation.

4. The process according to claim 1, wherein the product comprises acetic acid, and wherein step (v) comprises converting at least a portion of the acetic acid to ethanol.

5. The process according to claim 4, wherein step (v) comprises subjecting the acetic acid or an ester of the acetic acid to a hydrogenation reaction, wherein the hydrogenation reaction comprises a hydrogenation catalyst.

6. The process according to claim 5, wherein step (v) comprises adding ethanol to the acetic acid to provide ethyl acetate, and subjecting the ethyl acetate to the hydrogenation reaction.

7. The process according to claim 6, comprising recovering the ethyl acetate prior to the hydrogenation reaction, and wherein recovering the ethyl acetate comprises a reactive distillation.

8. The process according to claim 4, wherein converting at least a portion of the acetic acid to ethanol comprises subjecting the acetic acid to a gas fermentation that produces ethanol.

9. The process according to claim 8, wherein the gas fermentation comprises introducing hydrogen and carbon monoxide to a reactor.

10. The process according to claim 4, wherein step (v) comprises:
a) adding ethanol to an effluent of the wet oxidation to provide ethyl acetate;
b) recovering the ethyl acetate by distillation; and
c) subjecting the recovered ethyl acetate to a hydrogenation reaction to produce ethanol.

11. The process according to claim 4, wherein step (v) comprises converting the carbon dioxide to ethanol.

12. The process according to claim 1, wherein the product comprises carbon dioxide, and wherein step (v) comprises converting at least a portion of the carbon dioxide to ethanol.

13. The process according to claim 12, comprising collecting carbon dioxide from the wet oxidation, and wherein step (v) comprises feeding the collected carbon dioxide to a gas fermentation that produces ethanol, and acetic acid, or a combination thereof.

14. The process according to claim 13, wherein the gas fermentation produces acetic acid, and comprising subjecting the acetic acid produced by the gas fermentation to a hydrogenation reaction to produce ethanol.

15. The process according to claim 1, wherein converting at least a portion of the product to an alcohol comprises reforming a natural gas stream to provide a stream comprising hydrogen, and introducing the stream comprising hydrogen and the product to a reactor.

16. The process according to claim 15, comprising generating steam, electric power, or a combination thereof, from the wet oxidation, and using at least a predetermined amount of the steam, electric power, or a combination thereof in the process, the predetermined amount selected such that greenhouse gas emissions resulting from reforming the natural gas stream are at least compensated by greenhouse gas emission reductions provided by using the predetermined amount.

17. The process according to claim 1, wherein hydrolyzing at least a portion of the hemicellulose and cellulose in the lignocellulosic feedstock comprises pretreating the lignocellulosic feedstock with sulfur dioxide, sulfurous acid, or a combination thereof, and comprising recovering sulfate salts from an effluent of the wet oxidation.

18. The process according to claim 1, wherein (vi) comprises feeding a liquid comprising ethanol produced in (ii) and a liquid comprising ethanol produced in (v) to a distillation.

19. The process according to claim 1, comprising providing data supporting a net greenhouse gas life-cycle emission of the ethanol recovered in (vi) is lower than gasoline.

20. The process according to claim 19, wherein the net greenhouse gas life-cycle emission of the ethanol recovered in (vi) is at least 50% lower than gasoline.

21. The process according to claim 1, comprising generating a fuel credit for the ethanol recovered in (vi).

22. The process according to claim 1, comprising determining the life cycle greenhouse gas emissions for the ethanol recovered in (vi), said determining comprising calculating effects of at least one of heat, steam, and electricity generated as a result of the wet oxidation.

23. The process according to claim 1; wherein step (v) comprises:
a) collecting carbon dioxide from the wet oxidation, and feeding the collected carbon dioxide to a gas fermentation that produces acetic acid;
b) converting the acetic acid produced in the gas fermentation and acetic acid produced by the wet oxidation to ethanol.

* * * * *

UNITED STATES PATENT AND TRADEMARK OFFICE
CERTIFICATE OF CORRECTION

PATENT NO. : 10,513,715 B2
APPLICATION NO. : 15/762226
DATED : December 24, 2019
INVENTOR(S) : Foody et al.

It is certified that error appears in the above-identified patent and that said Letters Patent is hereby corrected as shown below:

On the Title Page

Column 2, Item (56), Line 3, under Other Publications, delete "Biotechnoogy," and insert --Biotechnology,--.

Column 2, Item (56), Line 11, under Other Publications, delete "applicaitons" and insert --applications--.

On page 2, Column 2, Item (56), Line 5, under Other Publications, delete "Capturing" and insert --"Capturing--.

On page 2, Column 2, Item (56), Line 5, under Other Publications, delete "Air," and insert --Air",--.

On page 2, Column 2, Item (56), Line 17, under Other Publications, delete "Hydrotalcite Like" and insert --Hydrotalcite-Like--.

In the Specification

In Column 2, Line 22, delete "base)" and insert --base),--.

In Column 3, Line 44, delete "example" and insert --example,--.

In Column 6, Line 40, delete "Lines." and insert --fines.--.

In Column 7, Line 28, delete "led" and insert --fed--.

In Column 8, Line 57, delete "case" and insert --ease--.

In Column 8, Line 66, delete "oxidant" and insert --oxidant,--.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,513,715 B2

In Column 10, Line 41, delete "strewn" and insert --stream--.

In Column 10, Line 62, delete "File" and insert --The--.

In Column 11, Line 6, delete "One" and insert --one--.

In Column 11, Line 17, delete "introduced" and insert --is introduced--.

In Column 13, Line 54, delete "One" and insert --one--.

In Column 14, Line 29, delete "lfungdahlii" and insert --ljungdahlii--.

In Column 16, Line 20, delete "olefin," and insert --olefin--.

In Column 17, Line 16, delete "led" and insert --fed--.

In Column 18, Line 17, delete "wet," and insert --wet--.

In Column 18, Line 30, delete "reaction, in" and insert --reaction. In--.

In Column 19, Line 18, delete "(Patrick. J." and insert --(Patrick J.--.

In Column 19, Line 58, delete "identification" and insert --Identification--.

In Column 20, Line 13, delete "and or" and insert --and/or--.

In Column 20, Line 48, delete "front" and insert --from--.

In Column 21, Line 4, delete "protein" and insert --protein,--.

In Column 22, Line 48, delete "60° C." and insert --160° C.--.

In Column 23, Line 34, delete "or" and insert --of--.

In Column 24, Line 57, delete "feedstock," and insert --feedstock--.

In Column 25, Line 57, delete "Myceliopthora," and insert --Myceliophthora,--.

In Column 25, Line 65, delete "or" and insert --of--.

In Column 26, Line 49, delete "or" and insert --of-- (first occurrence).

In Column 27, Line 50, delete "stiphis" and insert --stipitis--.

CERTIFICATE OF CORRECTION (continued)
U.S. Pat. No. 10,513,715 B2

In the Claims

In Column 33, Line 15, Claim 3, delete "claim 1;" and insert --claim 1,--.

In Column 34, Line 4, Claim 13, delete "and acetic acid," and insert --acetic acid,--.

In Column 34, Line 46 (Approx.), Claim 23, delete "claim 1;" and insert --claim 1,--.